US012800609B2

(12) United States Patent
Ruffaldi et al.

(10) Patent No.: US 12,800,609 B2
(45) Date of Patent: Nov. 17, 2026

(54) METHOD FOR DETECTING, BASED ON THE MEASUREMENT OR DETECTION OF ACCELERATIONS, OPERATING ANOMALIES OF AN UNCONSTRAINED MASTER DEVICE OF A MASTER-SLAVE ROBOTIC SYSTEM FOR MEDICAL OR SURGICAL TELEOPERATION AND RELATED ROBOTIC SYSTEM

(71) Applicant: MEDICAL MICROINSTRUMENTS, INC., Wilmington, DE (US)

(72) Inventors: Emanuele Ruffaldi, Pisa (IT); Massimiliano Simi, Pisa (IT)

(73) Assignee: MEDICAL MICROINSTRUMENTS, INC., Wilmington, DE (US)

( * ) Notice: Subject to any disclaimer, the term of this patent is extended or adjusted under 35 U.S.C. 154(b) by 55 days.

(21) Appl. No.: 18/546,182

(22) PCT Filed: Feb. 14, 2022

(86) PCT No.: PCT/IB2022/051293
§ 371 (c)(1),
(2) Date: Aug. 11, 2023

(87) PCT Pub. No.: WO2022/175802
PCT Pub. Date: Aug. 25, 2022

(65) Prior Publication Data

US 2024/0133916 A1 Apr. 25, 2024
US 2024/0230707 A9 Jul. 11, 2024

(30) Foreign Application Priority Data

Feb. 16, 2021 (IT) ........................ 102021000003416

(51) Int. Cl.
*A61B 34/37* (2016.01)
*A61B 34/00* (2016.01)
(Continued)

(52) U.S. Cl.
CPC .............. *G01P 15/18* (2013.01); *A61B 34/35* (2016.02); *A61B 34/77* (2016.02)

(58) Field of Classification Search
CPC ......... G01P 15/18; A61B 34/35; A61B 34/77; A61B 34/37; A61B 2034/2046;
(Continued)

(56) References Cited

U.S. PATENT DOCUMENTS

| | | |
|---|---|---|
| 5,943,914 A | 8/1999 | Morimoto |
| 6,063,095 A | 5/2000 | Wang |

(Continued)

FOREIGN PATENT DOCUMENTS

| | | |
|---|---|---|
| DE | 102010009065 A1 | 8/2011 |
| DE | 102014006264 A1 | 11/2015 |

(Continued)

OTHER PUBLICATIONS

International Search Report and Written Opinion received for PCT Serial No. PCT/IB2022/051226 on Apr. 8, 2022, 15 pgs.

(Continued)

*Primary Examiner* — Jaime Figueroa
(74) *Attorney, Agent, or Firm* — Merchant & Gould P.C.

(57) ABSTRACT

A method for identifies an anomaly condition in using a hand-held, mechanically unconstrained master device to control a robotic system for medical or surgical teleoperation. The method includes detecting and/or calculating, by sensors, the acceleration vector of a point belonging to or integral with a master device, or of a virtual point uniquely and rigidly associated with the master device; and then identifying a detectable anomaly condition based on a component or modulus of the detected and/or calculated acceleration vector. The detectable anomalies include one or more of the following: involuntary drop of the master device and/or excessive acceleration of the master device, and/or (Continued)

sudden and/or involuntary opening of the master device. Each of the detectable anomalies is associated with a system state change to be performed if the anomaly is detected. A master-slave robotic system for medical or surgical teleoperation is equipped to perform the method.

19 Claims, 8 Drawing Sheets

(51) Int. Cl.

| | |
|---|---|
| ***A61B 34/30*** | (2016.01) |
| ***A61B 34/35*** | (2016.01) |
| ***B25J 9/16*** | (2006.01) |
| ***B25J 19/02*** | (2006.01) |
| ***G01P 15/18*** | (2013.01) |

(58) Field of Classification Search

CPC .... A61B 2090/0801; A61B 2560/0276; A61B 2562/0219; A61B 34/74; A61B 34/30; A61B 90/06; A61B 2034/2048; B25J 9/1674; B25J 9/1689; B25J 19/02

USPC ................. 700/245–264; 318/568.11–568.25

See application file for complete search history.

(56) References Cited

U.S. PATENT DOCUMENTS

| | | | | |
|---|---|---|---|---|
| 6,364,888 | B1 * | 4/2002 | Niemeyer | A61B 34/37 348/E13.016 |
| 6,424,885 | B1 * | 7/2002 | Niemeyer | A61B 34/77 600/109 |
| 6,459,926 | B1 | 10/2002 | Nowlin | |
| 6,594,552 | B1 | 7/2003 | Nowlin | |
| 6,671,581 | B2 | 12/2003 | Niemeyer | |
| 6,766,204 | B2 | 7/2004 | Niemeyer | |
| 6,879,880 | B2 | 4/2005 | Nowlin | |
| 7,087,049 | B2 | 8/2006 | Nowlin | |
| 7,155,315 | B2 | 12/2006 | Niemeyer | |
| 7,331,967 | B2 | 2/2008 | Lee | |
| 7,373,219 | B2 | 5/2008 | Nowlin | |
| 7,778,733 | B2 | 8/2010 | Nowlin | |
| 7,806,891 | B2 | 10/2010 | Nowlin | |
| 7,886,743 | B2 | 2/2011 | Cooper | |
| 7,947,050 | B2 | 5/2011 | Lee | |
| 7,967,137 | B2 | 6/2011 | Fulbrook | |
| 8,004,229 | B2 * | 8/2011 | Nowlin | B25J 9/1689 318/568.2 |
| 8,005,571 | B2 | 8/2011 | Sutherland | |
| 8,123,740 | B2 | 2/2012 | Madhani | |
| 8,220,468 | B2 | 7/2012 | Cooper | |
| 8,281,670 | B2 * | 10/2012 | Larkin | A61B 34/30 73/862.045 |
| 8,368,649 | B2 | 2/2013 | Hall | |
| 8,375,808 | B2 * | 2/2013 | Blumenkranz | B25J 15/0009 73/862.044 |
| 8,521,331 | B2 | 8/2013 | Itkowitz | |
| 8,540,748 | B2 | 9/2013 | Murphy | |
| 8,543,240 | B2 | 9/2013 | Itkowitz | |
| 8,620,473 | B2 | 12/2013 | Diolaiti | |
| 8,638,057 | B2 | 1/2014 | Goldberg | |
| 8,677,820 | B2 | 3/2014 | Nakagawa | |
| 8,812,160 | B2 | 8/2014 | Hagn | |
| 8,831,782 | B2 | 9/2014 | Itkowitz | |
| 8,935,003 | B2 | 1/2015 | Itkowitz | |
| 8,939,963 | B2 | 1/2015 | Rogers | |
| 8,996,173 | B2 | 3/2015 | Itkowitz | |
| 9,060,796 | B2 | 6/2015 | Seo | |
| 9,101,379 | B2 | 8/2015 | Au | |
| 9,333,042 | B2 | 5/2016 | Diolaiti | |
| 9,387,043 | B2 * | 7/2016 | Yang | A61B 34/37 |
| 9,408,668 | B2 | 8/2016 | Durant | |
| 9,452,020 | B2 * | 9/2016 | Griffiths | A61B 90/06 |
| 9,492,927 | B2 | 11/2016 | Diolaiti | |
| 9,554,866 | B2 | 1/2017 | Cunningham | |
| 9,629,680 | B2 | 4/2017 | Winer | |
| 9,632,573 | B2 | 4/2017 | Ogawa | |
| 9,707,684 | B2 * | 7/2017 | Ruiz Morales | A61B 34/70 |
| 9,743,989 | B2 | 8/2017 | Itkowitz | |
| 9,770,300 | B2 | 9/2017 | Kwon | |
| 9,855,662 | B2 * | 1/2018 | Ruiz Morales | B25J 9/04 |
| 9,901,402 | B2 | 2/2018 | Itkowitz | |
| 9,949,799 | B2 * | 4/2018 | Hingwe | A61B 34/30 |
| 9,968,405 | B2 | 5/2018 | Cooper | |
| 10,013,082 | B2 | 7/2018 | Schecter | |
| 10,034,718 | B2 | 7/2018 | Griffiths | |
| 10,052,164 | B2 | 8/2018 | Overmyer | |
| 10,085,810 | B2 | 10/2018 | Vakharia | |
| 10,123,844 | B2 | 11/2018 | Nowlin | |
| 10,188,472 | B2 | 1/2019 | Diolaiti | |
| 10,219,870 | B2 | 3/2019 | Mondry | |
| 10,219,898 | B2 | 3/2019 | Forsell | |
| 10,271,915 | B2 | 4/2019 | Diolaiti | |
| 10,292,661 | B1 | 5/2019 | LaBorde | |
| 10,299,873 | B2 | 5/2019 | Hares | |
| 10,299,883 | B2 | 5/2019 | Kilroy | |
| 10,307,199 | B2 * | 6/2019 | Farritor | A61B 18/00 |
| 10,321,964 | B2 | 6/2019 | Grover | |
| 10,357,320 | B2 | 7/2019 | Beira | |
| 10,357,324 | B2 | 7/2019 | Flatt | |
| 10,376,323 | B2 | 8/2019 | Farritor | |
| 10,376,337 | B2 | 8/2019 | Kilroy | |
| 10,383,699 | B2 | 8/2019 | Kilroy | |
| 10,393,109 | B2 | 8/2019 | Wu | |
| 10,413,374 | B2 | 9/2019 | Chassot | |
| 10,420,618 | B2 | 9/2019 | Grover | |
| 10,470,830 | B2 | 11/2019 | Hill | |
| 10,485,621 | B2 | 11/2019 | Morrissette | |
| 10,512,514 | B2 | 12/2019 | Nowlin | |
| 10,512,515 | B2 | 12/2019 | Bailey | |
| 10,524,871 | B2 | 1/2020 | Liao | |
| 10,531,929 | B2 | 1/2020 | Widenhouse | |
| 10,543,050 | B2 | 1/2020 | Itkowitz | |
| 10,561,468 | B2 | 2/2020 | Cunningham | |
| 10,568,703 | B2 | 2/2020 | Nobles | |
| 10,568,704 | B2 | 2/2020 | Savall | |
| 10,603,123 | B2 | 3/2020 | Vakharia | |
| 10,617,484 | B2 | 4/2020 | Kilroy | |
| 10,624,708 | B2 | 4/2020 | Hunter | |
| 10,639,114 | B2 | 5/2020 | Schuh | |
| 10,653,489 | B2 | 5/2020 | Kopp | |
| 10,661,453 | B2 | 5/2020 | Koenig | |
| 10,736,701 | B2 | 8/2020 | Savall | |
| 10,736,706 | B2 | 8/2020 | Scheib | |
| 10,751,136 | B2 | 8/2020 | Farritor | |
| 10,758,298 | B2 | 9/2020 | Felder | |
| 10,779,898 | B2 | 9/2020 | Hill | |
| 10,786,327 | B2 | 9/2020 | Anderson | |
| 10,789,329 | B2 | 9/2020 | Lanting | |
| 10,813,713 | B2 | 10/2020 | Koch | |
| 10,820,953 | B2 | 11/2020 | Kralicky | |
| 10,842,577 | B2 | 11/2020 | Kilroy | |
| 10,842,581 | B2 | 11/2020 | Bailey | |
| 10,881,477 | B1 | 1/2021 | Genova | |
| 10,888,390 | B2 | 1/2021 | Higuchi | |
| 10,898,281 | B2 | 1/2021 | Cooper | |
| 10,912,618 | B2 | 2/2021 | Vakharia | |
| 10,959,798 | B2 | 3/2021 | Diolaiti | |
| 10,987,192 | B2 | 4/2021 | Garcia Kilroy | |
| 11,037,464 | B2 | 6/2021 | Ho | |
| 11,045,268 | B2 | 6/2021 | Grover | |
| 11,083,532 | B2 | 8/2021 | Liao | |
| 11,083,534 | B2 | 8/2021 | Hares | |
| 11,096,746 | B2 | 8/2021 | Savall | |
| 11,109,925 | B2 | 9/2021 | Cooper | |
| 11,135,031 | B2 | 10/2021 | Savall | |
| 11,172,997 | B2 | 11/2021 | Kostrzewski | |
| 11,179,209 | B2 | 11/2021 | Kralicky | |
| 11,179,211 | B2 | 11/2021 | Zemlok | |
| 11,179,213 | B2 | 11/2021 | Huang | |
| 11,213,364 | B2 | 1/2022 | Popovic | |
| 11,246,670 | B2 | 2/2022 | Swayze | |

(56) References Cited

U.S. PATENT DOCUMENTS 11,266,469 B2 * 3/2022 Fuerst ........................ B25J 9/16
11,284,957 B2 3/2022 Denlinger
11,284,959 B2 3/2022 Bailey
11,344,374 B2 5/2022 Tekiela
11,357,597 B2 6/2022 Jhaveri
11,399,908 B2 8/2022 Diolaiti
11,406,465 B2 8/2022 Zemlok
11,439,478 B2 9/2022 Anderson
11,446,097 B2 9/2022 Savall
11,457,987 B2 10/2022 He
11,478,318 B2 10/2022 Cone
11,478,928 B2 10/2022 Hariri
11,484,379 B2 11/2022 Sutherland
11,504,197 B1 11/2022 Noonan
11,504,203 B2 11/2022 Flatt
11,534,246 B2 * 12/2022 Fuerst .................... B25J 13/087
11,534,252 B2 12/2022 DiMaio
11,576,733 B2 2/2023 Anglese
11,607,279 B2 3/2023 Chaplin
11,666,401 B2 6/2023 Denlinger
11,684,434 B2 6/2023 Shelton
11,707,336 B2 7/2023 Itkowitz
11,712,314 B2 8/2023 Thompson
12,048,505 B2 7/2024 Thompson
2002/0055795 A1 5/2002 Niemeyer
2002/0128552 A1 * 9/2002 Nowlin .................. A61B 34/35 600/427
2003/0004610 A1 1/2003 Niemeyer
2003/0195664 A1 10/2003 Nowlin
2004/0039485 A1 2/2004 Niemeyer
2005/0194507 A1 9/2005 White
2006/0030840 A1 2/2006 Nowlin
2006/0106493 A1 5/2006 Niemeyer
2006/0241414 A1 10/2006 Nowlin
2007/0013336 A1 1/2007 Mowlin
2008/0114494 A1 5/2008 Nixon
2008/0154246 A1 6/2008 Nowlin
2009/0301927 A1 12/2009 Fulbrook
2010/0053085 A1 3/2010 Hall
2010/0094312 A1 * 4/2010 Ruiz Morales ........ A61B 34/70 73/504.03
2010/0274087 A1 * 10/2010 Diolaiti .................. A61B 34/71 600/407
2011/0118748 A1 * 5/2011 Itkowitz ................. A61B 90/98 606/130
2012/0011932 A1 1/2012 Nakagawa
2012/0059391 A1 3/2012 Diolaiti
2012/0071891 A1 3/2012 Itkowitz
2012/0071892 A1 3/2012 Itkowitz
2012/0316681 A1 12/2012 Hagn
2013/0012930 A1 * 1/2013 Ruiz Morales ........ A61B 34/76 606/1
2013/0035697 A1 2/2013 Ogawa
2013/0316681 A1 11/2013 Huang
2013/0321262 A1 12/2013 Schecter
2014/0018960 A1 1/2014 Itkowitz
2014/0160015 A1 6/2014 Ogawa
2014/0171964 A1 * 6/2014 Yang ...................... A61B 34/37 606/130
2014/0222021 A1 8/2014 Diolaiti
2015/0025549 A1 1/2015 Kilroy
2015/0038981 A1 2/2015 Kilroy
2015/0038982 A1 2/2015 Kilroy
2015/0066051 A1 3/2015 Kwon
2015/0080909 A1 3/2015 Itkowitz
2015/0157410 A1 6/2015 Kilroy
2015/0182289 A1 7/2015 Itkowitz
2016/0242860 A1 8/2016 Diolaiti
2016/0287279 A1 10/2016 Bovay
2017/0035521 A1 2/2017 Diolaiti
2017/0086931 A1 3/2017 Auld
2017/0095295 A1 4/2017 Overmyer
2017/0095298 A1 4/2017 Vakharia
2017/0156806 A1 6/2017 Prisco
2017/0224428 A1 8/2017 Kopp
2017/0252112 A1 9/2017 Crawford
2017/0265949 A1 9/2017 Crawford
2017/0312043 A1 11/2017 Ogawa
2017/0319284 A1 11/2017 Itkowitz
2018/0025666 A1 1/2018 Ho
2018/0036088 A1 * 2/2018 Kilroy ..................... G06F 3/017
2018/0078034 A1 3/2018 Savall
2018/0078319 A1 3/2018 Nobles
2018/0078321 A1 * 3/2018 Liao ....................... B25J 9/1689
2018/0092706 A1 4/2018 Anderson
2018/0161108 A1 6/2018 Savall
2018/0168681 A1 6/2018 Kirk
2018/0168759 A1 6/2018 Kilroy
2018/0194013 A1 * 7/2018 Ruiz Morales ........ A61B 34/35
2018/0214223 A1 8/2018 Turner
2018/0235719 A1 8/2018 Jarc
2019/0012006 A1 1/2019 Schecter
2019/0029770 A1 1/2019 Bailey
2019/0069960 A1 3/2019 Vakharia
2019/0110847 A1 4/2019 Diolaiti
2019/0142530 A1 5/2019 Thompson
2019/0201152 A1 7/2019 Diolaiti
2019/0239972 A1 * 8/2019 Chassot ................. A61B 34/77
2019/0307524 A1 10/2019 Popovic
2019/0314097 A1 10/2019 Diolaiti
2019/0343594 A1 11/2019 Garcia Kilroy
2019/0380791 A1 12/2019 Fuerst
2019/0380802 A1 12/2019 Savall
2019/0380809 A1 12/2019 Fuerst
2020/0008901 A1 1/2020 Garcia Kilroy
2020/0015918 A1 1/2020 Payyavula
2020/0022775 A1 1/2020 Garcia Kilroy
2020/0046439 A1 2/2020 Tekiela
2020/0046450 A1 2/2020 Tsao
2020/0069388 A1 3/2020 Bailey
2020/0085522 A1 3/2020 Liao
2020/0113641 A1 4/2020 Itkowitz
2020/0138534 A1 * 5/2020 Garcia Kilroy ........ A61G 13/08
2020/0179068 A1 6/2020 Peine
2020/0194117 A1 6/2020 Krieger
2020/0197112 A1 6/2020 Chin
2020/0197115 A1 6/2020 Vakharia
2020/0205922 A1 7/2020 Cone
2020/0214773 A1 7/2020 Nobles
2020/0214778 A1 7/2020 Turner
2020/0214779 A1 7/2020 Masuda
2020/0222124 A1 7/2020 Savall
2020/0222134 A1 7/2020 Schuh
2020/0275985 A1 9/2020 Thompson
2020/0289212 A1 9/2020 Savall
2020/0289223 A1 9/2020 Denlinger
2020/0330170 A1 10/2020 Farritor
2020/0360096 A1 11/2020 Savall
2020/0360097 A1 11/2020 DiMaio
2020/0390510 A1 12/2020 Thompson
2020/0397517 A1 12/2020 Unsworth
2020/0397529 A1 12/2020 Anderson
2020/0405408 A1 12/2020 Shelton
2020/0405434 A1 12/2020 Schuh
2021/0030495 A1 2/2021 Savall
2021/0052338 A1 2/2021 Hill
2021/0052341 A1 2/2021 Bailey
2021/0059781 A1 3/2021 Peine
2021/0085301 A1 3/2021 Au
2021/0121260 A1 4/2021 Genova
2021/0153964 A1 5/2021 Diolaiti
2021/0153965 A1 5/2021 Lau
2021/0153966 A1 5/2021 Lau
2021/0196411 A1 7/2021 Vakharia
2021/0196413 A1 7/2021 Inoue
2021/0197401 A1 7/2021 Weintraub
2021/0236220 A1 8/2021 Diolaiti
2021/0290326 A1 9/2021 Diolaiti
2021/0290328 A1 9/2021 Miller
2021/0298855 A1 9/2021 Thompson
2021/0304639 A1 9/2021 Ho
2021/0322117 A1 10/2021 Liao
2021/0322119 A1 10/2021 Hares

(56) References Cited

U.S. PATENT DOCUMENTS

| | | | |
|---|---|---|---|
| 2021/0353381 | A1 | 11/2021 | Usui |
| 2021/0369365 | A1 | 12/2021 | Goswami |
| 2022/0015839 | A1 | 1/2022 | Savall |
| 2022/0015852 | A1 | 1/2022 | Savall |
| 2022/0031415 | A1 | 2/2022 | Vargas |
| 2022/0047345 | A1 | 2/2022 | Choi |
| 2022/0096189 | A1 | 3/2022 | Popovic |
| 2022/0184823 | A1 | 6/2022 | Bonny |
| 2022/0192763 | A1 | 6/2022 | Fuerst |
| 2022/0202437 | A1 | 6/2022 | Overmyer |
| 2022/0211452 | A1 | 7/2022 | Clark |
| 2022/0218418 | A1 | 7/2022 | Jolaeimoghaddam |
| 2022/0226056 | A1 | 7/2022 | Beckman |
| 2022/0265380 | A1 | 8/2022 | Bailey |
| 2022/0361736 | A1 | 11/2022 | Danna |
| 2022/0361970 | A1 | 11/2022 | Griffiths |
| 2022/0370163 | A1 | 11/2022 | Schuh |
| 2022/0378526 | A1 | 12/2022 | Balicki |
| 2022/0378527 | A1 | 12/2022 | Basafa |
| 2022/0378533 | A1 | 12/2022 | McDiarmid |
| 2022/0387131 | A1 | 12/2022 | Anderson |
| 2022/0395346 | A1 | 12/2022 | Ihara |
| 2022/0401162 | A1 | 12/2022 | Unsworth |
| 2023/0028689 | A1 | 1/2023 | Rabindran |
| 2023/0045591 | A1 | 2/2023 | de la Fuente Klein |
| 2023/0149105 | A1 | 5/2023 | Thornycroft |
| 2023/0301738 | A1 | 9/2023 | Thompson |
| 2023/0355261 | A1 | 11/2023 | Yu |

FOREIGN PATENT DOCUMENTS

| | | | |
|---|---|---|---|
| EP | 2845556 | A1 | 3/2015 |
| EP | 3245975 | A1 | 11/2017 |
| EP | 3424651 | A1 | 1/2019 |
| EP | 3459429 | A1 | 3/2019 |
| EP | 3574860 | A1 | 12/2019 |
| EP | 3852668 | | 7/2021 |
| JP | 2013034835 | | 2/2013 |
| JP | 2013049121 | | 3/2013 |
| JP | 2013510671 | | 3/2013 |
| JP | 2013510672 | | 3/2013 |
| JP | 2016512733 | | 5/2016 |
| JP | 2016514492 | | 5/2016 |
| JP | 2017099820 | | 6/2017 |
| JP | 2019536556 | A | 12/2019 |
| JP | 2020529237 | A | 10/2020 |
| JP | 2021162200 | | 10/2021 |
| WO | 2013018861 | | 2/2013 |
| WO | 2013071071 | A1 | 5/2013 |
| WO | 2014151621 | A1 | 9/2014 |
| WO | 2016053657 | A1 | 4/2016 |
| WO | 2016171757 | A1 | 10/2016 |
| WO | 2016201207 | A1 | 12/2016 |
| WO | 2017094844 | A1 | 6/2017 |
| WO | 2018104252 | A1 | 6/2018 |
| WO | 2018107062 | A1 | 6/2018 |
| WO | 2019027922 | A1 | 2/2019 |
| WO | 2019050878 | A2 | 3/2019 |
| WO | 2019099584 | A1 | 5/2019 |
| WO | 2019103954 | A1 | 5/2019 |
| WO | 2019220407 | A1 | 5/2019 |
| WO | 2019220408 | A1 | 5/2019 |
| WO | 2019220409 | A1 | 5/2019 |
| WO | 20200092170 | A1 | 10/2019 |
| WO | 2019240825 | A1 | 12/2019 |
| WO | 2020139405 | A1 | 7/2020 |
| WO | 2020153411 | A1 | 7/2020 |
| WO | 2021141920 | A1 | 7/2021 |
| WO | 2021188127 | A1 | 9/2021 |
| WO | 2022155067 | A1 | 7/2022 |

OTHER PUBLICATIONS

International Search Report and Written Opinion received for PCT Serial No. PCT/IB2022/051286 on Jun. 7, 2022, 13 pgs.

International Search Report and Written Opinion received for PCT Serial No. PCT/IB2022/051293 on Apr. 8, 2022, 16 pgs.

International Search Report and Written Opinion received for PCT Serial No. PCT/IB2022/051321 on Jun. 8, 2022, 16 pgs.

International Search Report and Written Opinion received for PCT Serial No. PCT/IB2022/051328 on Jun. 13, 2022, 16 pgs.

International Search Report and Written Opinion received for PCT Serial No. PCT/IB2022/051279 on Jun. 13, 2022, 15 pgs.

International Search Report and Written Opinion received for PCT Serial No. PCT/IB2022/051244 on Jun. 7, 2022, 13 pgs.

* cited by examiner

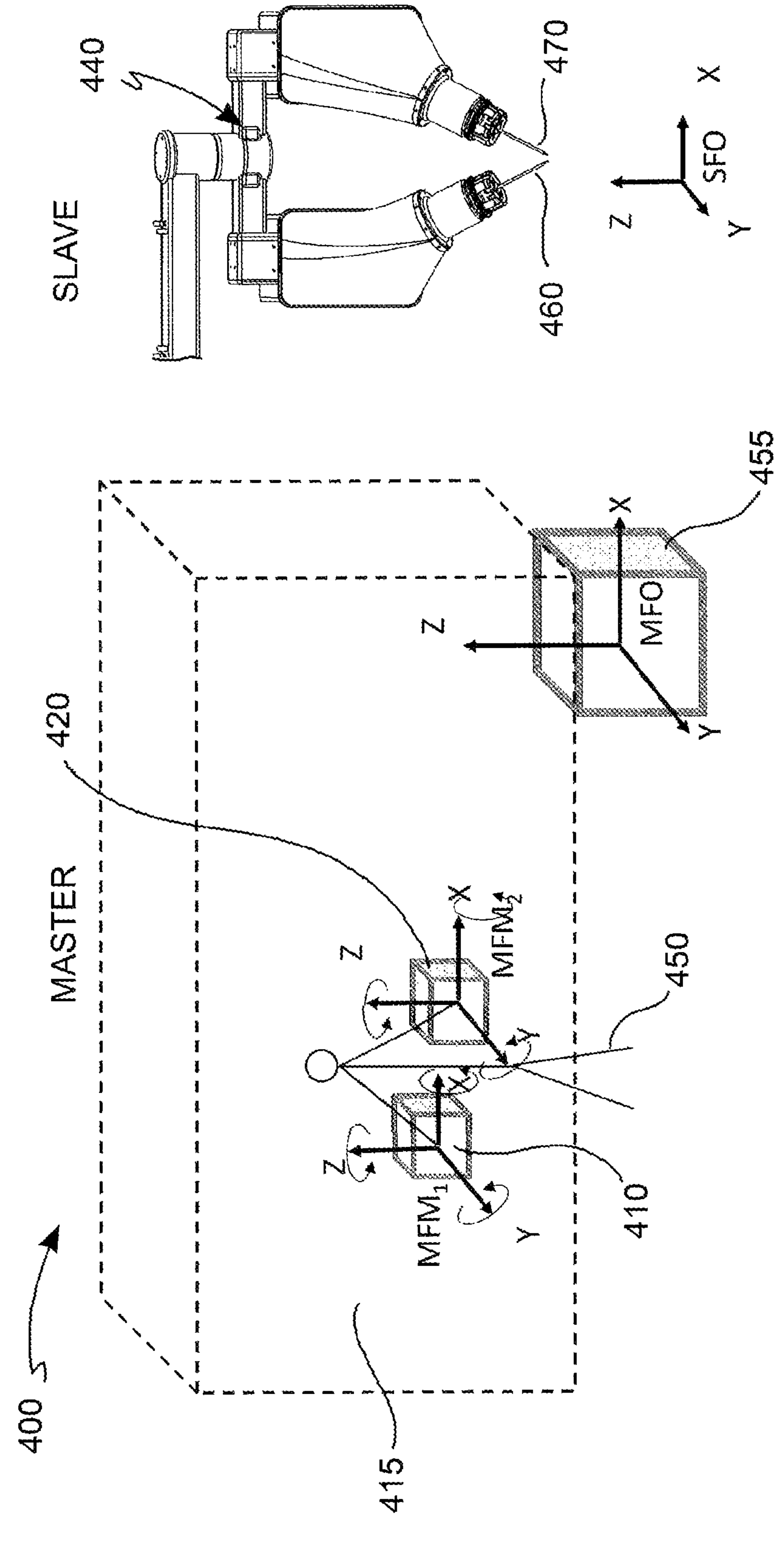
FIG. 4bis

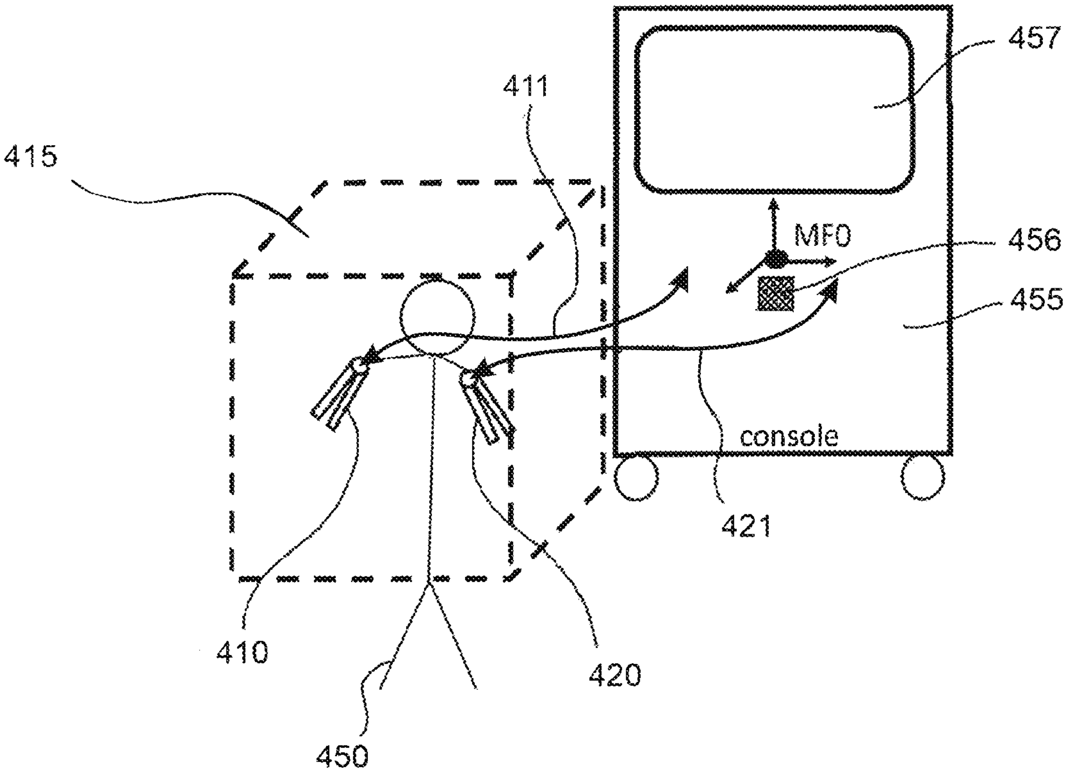
FIG. 4ter

S16A

METHOD FOR DETECTING, BASED ON THE MEASUREMENT OR DETECTION OF ACCELERATIONS, OPERATING ANOMALIES OF AN UNCONSTRAINED MASTER DEVICE OF A MASTER-SLAVE ROBOTIC SYSTEM FOR MEDICAL OR SURGICAL TELEOPERATION AND RELATED ROBOTIC SYSTEM

CROSS-REFERENCE TO RELATED APPLICATIONS

The present application is a National Stage Filing of PCT International Application No. PCT/IB2022/051293 filed on Feb. 14, 2022, which claims priority to Italian Patent Application No. 102021000003416, filed on Feb. 16, 2021, which is incorporated herein by reference in its entirety.

TECHNOLOGICAL BACKGROUND OF THE INVENTION

Field of Application

The present invention relates to a method for detecting operating anomalies of an unconstrained master device of a master-slave robotic system for medical or surgical teleoperation, and a corresponding master-slave robotic system for medical or surgical teleoperation equipped so as to perform the aforesaid method.

Description of the Prior Art

In the context of robotic teleoperated surgery, in the presence of master-slave robotic systems for medical or surgical teleoperation, it is very important to evaluate in real time whether the master device which imparts the movement to the slave is functioning well and operates in the expected conditions, adapted to ensure effective action and patient safety, and it is also important to verify in real time that the master device is not operating in abnormal conditions or situations.

This need is felt both in the context of master devices with an unconstrained, magnetically or optically detected interface, and in the context of master devices with a mechanically constrained interface.

In the context of mechanically unconstrained or "ungrounded" master devices (recently emerged as an effective and advantageous solution, as for example shown in documents WO-2019-220407, WO-2019-220408 and WO-2019-220409 of the same Applicant) the aforesaid requirement poses complex technical challenges.

In particular, in a master-slave robotic system, in which the master is not mechanically constrained or motorized, the transmission of unintentional commands to the surgical (or micro-surgical) device, deriving from an uncontrolled operating situation of the master device, must be prevented to avoid risks for the patient. Examples of such solutions having an unconstrained master are shown by documents US-2011-118748, in which the master is worn by the surgeon, and WO-2020-0092170, in which the master body has a substantially oval shape.

The known robotic master-slave systems for medical or surgical teleoperation, with a mechanically unconstrained (or "ungrounded" or "groundless") master device, do not provide fully satisfactory solutions to the aforesaid needs, especially taking into account the very stringent safety requirements which derive from the fact that any anomaly in the operation or condition of the master device can identify consequent anomalies in the operation of the slave device and the surgical instrument associated therewith, intended to act on the patient, with possible even serious consequences on the patient.

Therefore, in this context, the need is strongly felt to apply procedures for verifying any abnormal operating conditions of the master device in real time, conducted automatically by the robot control system for medical or surgical teleoperation, such as to be are efficient and reliable, in order to meet the stringent safety requirements which are required by such applications.

SUMMARY OF THE INVENTION

It is the object of the present invention to provide a method for detecting operating anomalies of a master device of a robotic master-slave system for medical or surgical teleoperation, which allows at least partially overcoming the drawbacks mentioned above with reference to the prior art, and responding to the needs mentioned above particularly felt in the technical field considered.

It is another object of the present invention to provide a method for managing anomalies detected in a master device comprising carrying out the method for detecting anomalies of the master device.

It is also an object of the present invention to provide a robotic system for medical or surgical teleoperation equipped to perform the aforesaid anomaly detection method.

BRIEF DESCRIPTION OF THE DRAWINGS

Further features and advantages of the system and method according to the invention will become apparent from the following description of preferred embodiments, given by way of indicative, non-limiting examples, with reference to the accompanying drawings, in which:

FIGS. 4 and 4*bis* diagrammatically show a teleoperated surgery system, according to some embodiments;

FIG. 4*ter* diagrammatically shows a portion of a teleoperated surgery system, according to an embodiment;

DETAILED DESCRIPTION

Figure 1:
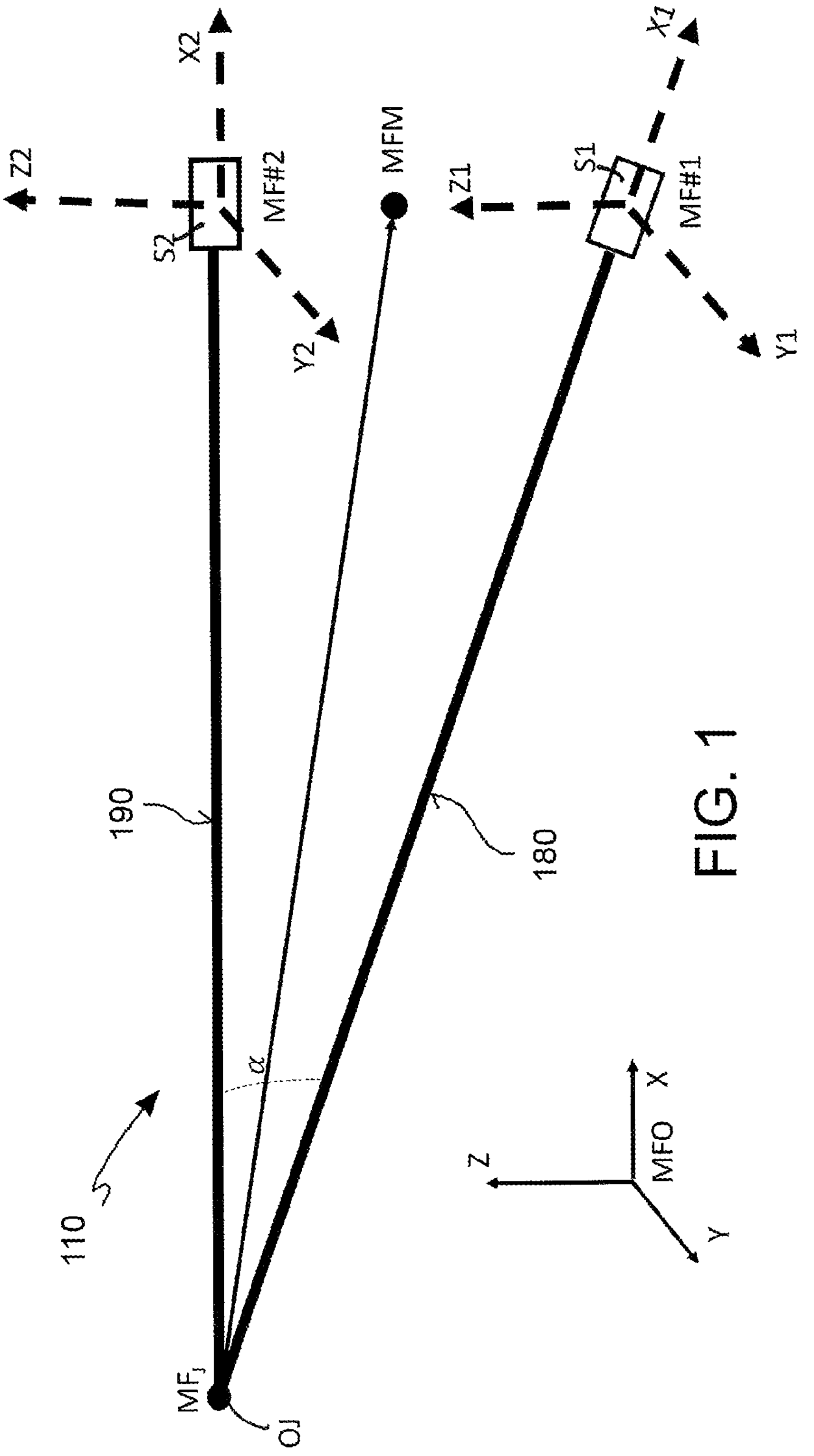
FIGS. 1 and 2(*a*)-2(*b*) show geometric parameters and reference frames used in the method of the present invention, applied to an embodiment of the master device with a "gripper" structure.

With reference to FIGS. 1-9, a method is described for identifying and recognizing and/or discriminating at least one anomaly/fault condition in the use of a hand-held master device, intended to be held in hand by the operator, and mechanically ungrounded, used to control a robotic system for medical or surgical teleoperation.

Such a method comprises the steps of detecting and/or calculating, by one or more sensors, the acceleration vector of at least one point belonging to or integral with the master device, or of a virtual point uniquely and rigidly associated with the master device; and then identifying and recognizing and/or discriminating at least one detectable anomaly/fault condition based on at least one component or modulus of said detected and/or calculated acceleration vector.

The aforesaid detectable anomalies/faults comprise at least one of the following: involuntary drop of the master device and/or excessive acceleration of the master device and/or sudden and/or involuntary opening of the master device.

Furthermore, each of the detectable anomalies/faults is associated with at least one system state change to be performed if the anomaly/fault is detected.

According to an implementation option of the method, the aforesaid system state change, to be performed if an anomaly is detected, comprises exiting the teleoperation.

According to an implementation option, the identifying step comprises identifying the at least one detectable anomaly condition based on at least one component of the aforesaid detected and/or calculated acceleration vector.

According to an implementation option, the identifying step comprises identifying the at least one detectable anomaly condition based on the modulus of the aforesaid detected and/or calculated acceleration vector.

In accordance with an embodiment, the method comprises the further step of measuring and/or detecting, by one or more sensors, the position vector of said at least one point belonging to or integral with the master device and the evolution over time of such a position vector.

In such a case, the step of detecting and/or calculating said acceleration vector comprises detecting and/or calculating the acceleration vector based on the evolution over time of the respective measured and/or detected position vector.

According to an implementation option of such an embodiment, the aforesaid step of detecting and calculating the acceleration vector comprises calculating the acceleration vector by movable windows of N samples of the vector representing the position vector evolution over time, and by interpolation with second order polynomials, for the degree of freedom related to the grip, and with third order polynomials, for the degrees of freedom related to the master device translation and orientation.

According to another implementation option of such an embodiment, the aforesaid step of detecting and calculating the acceleration vector comprises calculating the acceleration vector by a Kalman-type predictive filter which uses a movement model with random acceleration dynamics adapted to estimate the master device position state and correct the estimate based on information provided by the measurement system. Such a model is preferably parameterized with regard to the process noise thereof, and with regard to the noise of the measurements.

According to a further implementation option of such an embodiment, which combines a predictive approach with that of delayed smoothing, the method considers a window of N samples, predicts forward to the end of the window, and then corrects the prediction in the past to the point in the center of the window.

Kalman's filter-based solution, with respect to the polynomial fitting option, has the potential to adapt to different observation noise values, but may be subject to an adaptation time of the filter to the input values.

In accordance with an implementation option, the acceleration is calculated based on the detection of the velocity vector and the evolution over time of the velocity vector.

According to an implementation option, the acceleration is directly detected by one or more sensors, in which such one or more sensors are accelerometers.

According to various possible embodiments of the method, as a basis for detecting anomalies, for each of the aforesaid at least one points belonging to or integral with the master device, or virtual point uniquely and rigidly associated with the master device, the linear acceleration and/or the angular acceleration and/or the linear velocity and/or the angular velocity and/or the position in Cartesian coordinates and/or the position in polar or angular coordinates are calculated or detected.

In accordance with a method embodiment, the aforesaid step of detecting and/or calculating the acceleration vector comprises detecting and/or calculating by at least two sensors the acceleration vector of each of at least two points belonging to or integral with the master device; and then calculating the acceleration vector of a virtual point uniquely and rigidly associated with the master device, corresponding to the midpoint between the points where the sensors are located.

For example, in a "gripper" master device, such a midpoint can be located on the opening circumference arc described by the one or more sensors of the "gripper" master device.

If there is only one control point, 6 degrees of freedom, i.e., 3 degrees of position and 3 degrees of orientation, can be detected.

If two control points are provided, it is also possible to detect a seventh degree of freedom, associated with the grip, representative of the opening/closing angle of the master device body.

In accordance with an embodiment, the method is performed in the context of a robotic system for medical or surgical teleoperation comprising the aforesaid master device and slave device, and further comprising a control unit.

The master device is mechanically ungrounded and adapted to be held in hand by a surgeon during surgery, and is configured to detect a manual command of the surgeon and generate a respective first electrical command signal.

The at least one slave robotic assembly comprises at least one slave surgical instrument configured to operate on the anatomy of a patient, in a manner controlled by the master device.

The control unit provided with a computer is configured to receive the aforesaid first electrical command signal from the master device, generate a second electrical command signal, based on the first electrical command signal, and provide the second electrical command signal to the slave robotic assembly, to actuate the at least one slave surgical instrument.

Furthermore, the control unit is operatively connected to the aforesaid one or more sensors to receive at least a third electrical signal representative of the detected and/or measured acceleration vector and/or the related evolution over time, and is configured to perform the aforesaid steps of calculating and detecting at least one detectable anomaly.

According to an implementation option, said third electrical signal corresponds to said first electrical signal.

According to a method embodiment, the aforesaid step of measuring and/or detecting is performed with respect to a reference coordinate frame associated with the robotic system for teleoperated surgery, and having predetermined axes and origin in a predetermined point.

For example, a fixed set of three Cartesian coordinates x, y, z is defined, having an origin O in a preset point.

In particular, according to a method embodiment, in which the robotic system for medical or surgical teleoperation comprises an operating console, the aforesaid reference coordinate frame is integral with the robotic system console.

In a method embodiment, such an operating console comprising at least one surgical chair comprising at least one seating surface for the surgeon to sit on during surgery, the aforesaid reference coordinate frame is integral with the aforesaid at least one surgical chair, for example with the seat of the surgical chair. The reference coordinate frame can be integral with a support for the seat of the surgical chair, the seat being rotatable with respect to the support for the seat.

According to an embodiment, the robotic system for medical or surgical teleoperation comprises a tracking system, which is suitable for detecting the input position and orientation of the master device within a predetermined tracking volume, so that the actuation of the slave surgical instrument depends on the manual command given by the surgeon by means of the master device and/or on the position and orientation of the master device within the tracking volume.

In a method embodiment, said operating console comprises at least one display which displays the slave workspace.

The operating console can be a console which is remote with respect to the slave device, or it can be a console located in the operating room together with the slave device.

In accordance with a method embodiment, the said step of measuring and/or detecting is performed by one or more magnetic sensors.

Each of the magnetic sensors is arranged at a respective one of the at least one point belonging to or integral with the master device, and is configured to detect a local value of a magnetic field generated by a magnetic field generator constrained to a part of the robotic system for teleoperated surgery.

In such a case, the reference coordinate frame originates at the aforesaid magnetic emitter, and has three orthogonal axes x, y, z.

According to an implementation option, said magnetic field generator belongs to sais tracking system.

In accordance with another method embodiment, the aforesaid step of measuring and/or detecting is performed by at least one optical sensor or camera, associated with and/or constrained to the robotic system for medical or surgical teleoperation. Multiple cameras can be included in stereoscopic configuration.

In such a case, the aforesaid reference coordinate frame is an internal reference coordinate system of the optical sensor or camera.

According to different possible implementation options of the embodiment disclosed above, the aforesaid at least one optical sensor or camera is constrained to and/or integral with the surgical chair, and/or is mounted on a support which is wearable by the surgeon, so as to be integral with the surgeon.

According to a method embodiment, in which the master device is a hand-held, unconstrained master device, comprising two rigid parts constrained to relatively rotate or translate with respect to a common axis, the aforesaid step of detecting and/or calculating comprises detecting and/or calculating, by respective sensors, the acceleration vector and/or the acceleration vector evolution over time, of at least two detectable points, a first point belonging to or integral with one of the aforesaid rigid parts of the master device and a second point belonging to or integral with the other one of the aforesaid rigid parts of the device.

In fact, the method can be applied, for example, to a master device having a "gripper" structure (shown for example in FIGS. 1 and 2) having two rigid parts constrained, elastically, to rotate with respect to a common transverse axis, orthogonal to the longitudinal extension of at least one (or both) of the aforesaid rigid parts of the master device.

The method can also be applied, for example, to a master device having a "pen" structure, having two rigid parts constrained, elastically, to translate along a longitudinal axis coinciding with the longitudinal extension of at least one (or both) of the aforesaid parts of the master device.

According to various possible embodiments of the method, said calculating step comprises calculating the acceleration vector and/or the velocity vector of said at least two detectable points, or calculating the acceleration vector and/or the velocity vector of one of said at least two detected points.

According to further implementation options, said calculating step further comprises calculating the acceleration vector and/or the velocity vector and/or the position vector of at least one of the following further points: midpoint between said two detected points and/or center of gravity of said master device, and/or of a master device rotational joint, and/or of a master device prismatic joint.

In accordance with a method embodiment, in which the master device body comprises two tips or free ends, a first tip or free end belonging to or integral with one of the rigid parts of the master device and a second tip or free end belonging to or integral with the other of the rigid parts of the device, the aforesaid two detectable points correspond to and/or are associated with a respective one of the aforesaid two tips or free ends of the master device.

In accordance with a method embodiment, in which the detectable anomaly/fault is an involuntary drop of the master device, the method comprises the following steps:

- detecting and/or calculating the vertical acceleration component ay, parallel to the gravity axis, of at least one of the two detected points;
- comparing the detected or calculated vertical acceleration component ay with a vertical acceleration threshold ay_thr;
- identifying the anomaly/fault associated with the involuntary drop of the master device if the aforesaid vertical acceleration component ay is greater than the aforesaid vertical acceleration threshold (ay_thr), according to the relation: ay>ay_thr.

According to an implementation option the vertical acceleration threshold value ay_thr is equal to the gravity acceleration g, or is a value around g (e.g., 80% of g).

According to an implementation option, the acceleration vector of each of the aforesaid at least two detection points of the master device is calculated to provide redundancy and/or a further verification.

In fact, the consistency of the calculated acceleration measurement of the aforesaid at least two points makes it possible to improve the estimation of the anomaly determination, further reducing the time window necessary for the estimation process.

An inconsistency of the calculated measurement of acceleration of the two points can be associated with a drop with rotation of the master device, or the breakage of the rigid constraints between the two sensors.

In the specific case of mounting two sensors in the same mechanical part of the master device, the behavior of the measurements is pure redundancy.

With reference to what has been described above, according to an implementation option, in order to detect a drop of the master device from the surgeon's hand, it is possible to rely on the information of the acceleration and/or the velocity component of the master device facing downwards.

With reference to what has been described above, according to an implementation option, the master device having two rigid parts constrained to each other to rotate about a common axis, said rigid parts being elastically biased to relatively move away, in order to detect a drop of the master device from the surgeon's hand it is possible to rely on detecting an involuntary opening of the master device i.e., detecting a relative distancing movement between the two rigid parts determined by the elastic biasing action. The detection of the involuntary opening can be obtained by information on angular velocity, and/or angular acceleration, and/or linear velocity, and/or linear acceleration.

According to an implementation option, the drop of the master device is detected using information on the relation between the accelerations of two sensors, said two sensors being respectively associated with the two rigid parts of the master device. For example, a relation function between the accelerations of the two sensors can compare the relative direction between the accelerations. According to an implementation option, the relation function processes the scalar product between the two acceleration vectors of the respective sensors to give an indication of the drop of the master device; in such an implementation option, it is possible to resort to a polynomial estimator of the position or the evolution of the position over time of the scalar product between the two sensors, said polynomial estimator having peaks at the drop event of the master device.

Figure 9:
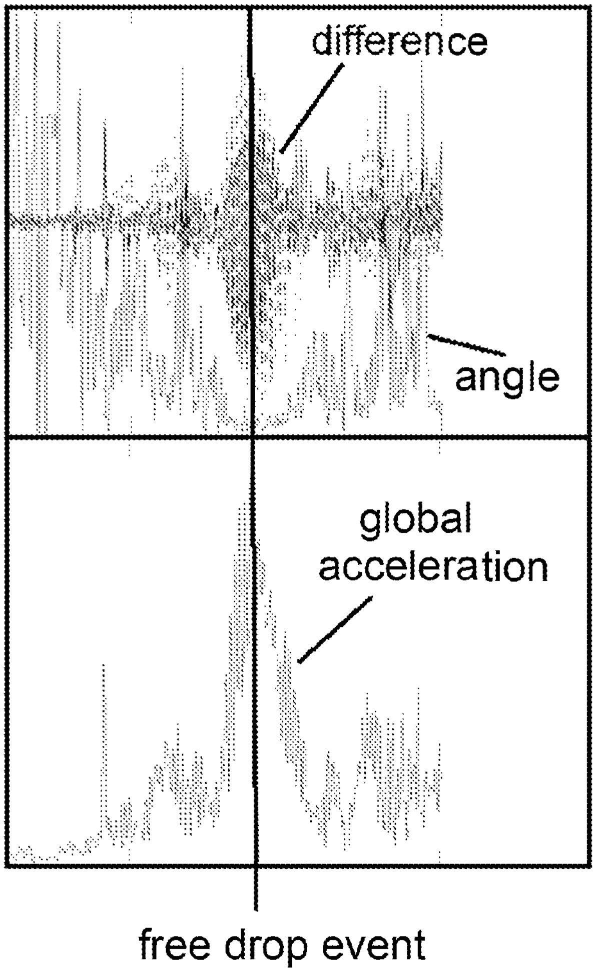
FIG. 9 is a graph diagrammatically showing the detection of the involuntary drop of the master device.

According to an implementation option as diagrammatically shown in FIG. 9, the master device having two rigid parts constrained to rotate about a common axis, said rigid parts being elastically biased to relatively move away, during the drop of the master device two phenomena occur (i) involuntary opening of the master device, and (ii) inertial rotation of the master device. Therefore, the acceleration vectors of the respective (detected and/or calculated) sensors have at least one transient of limited duration (but also for the entire duration of the drop in some cases) a first component facing downwards and a second component that can be attributed to the inertial rotation of the master device.

In such an implementation option, the detected angle between the two acceleration vectors is very low, for example minimum, at the drop; the evaluation of the residual oscillations given by the difference between the acceleration vectors of the respective sensors are very high (for example maximum). In other words, the angle between the acceleration vectors of the two sensors when very low (e.g., minimum) indicates a high degree of consistency between the accelerations in the specific case when both facing downwards; a high degree of fluctuation in the comparison (difference) between the two acceleration vectors indicates a drop event.

According to an implementation option, the master device having two rigid parts constrained to rotate about a common axis, said rigid parts being elastically biased to relatively move away, during the drop of the master device two phenomena occur (i) involuntary opening of the master device, and (ii) inertial rotation of the master device; therefore the velocity vectors of the respective (detected and/or calculated) sensors have at least one transient of limited duration (but also for the entire duration of the drop in some cases) a first component facing downwards and a second component that can be attributed to the inertial rotation of the master device.

In such an implementation option, the detected angle between the two velocity vectors is very low, for example minimum, at the drop; the evaluation of the residual oscillations given by the difference between the velocity vectors of the respective sensors are very high (for example maximum). In other words, the angle between the velocity vectors of the two sensors when very low (e.g., minimum) indicates a high degree of consistency between the velocities in the specific case when both facing downwards; a high degree of fluctuation in the comparison (difference) between the two velocity vectors indicates a drop event.

In accordance with a method embodiment, in which the detectable anomaly/fault is an excessive acceleration of the master device (e.g., imparted in the handling by the user), the method comprises the following steps:

detecting and/or calculating the acceleration vector modulus atot of at least one of the aforesaid at least two detected points;

comparing the detected and/or calculated acceleration vector modulus atot with a total acceleration threshold atot_thr;

detecting the anomaly/fault associated with an excessive acceleration of the master device if the aforesaid acceleration vector modulus atot is greater than the aforesaid total acceleration threshold atot_thr, according to the relation: atot>atot_thr.

According to an implementation option, said vertical acceleration threshold ay_thr is lower than said total acceleration threshold atot_thr.

For example, the relation "atot=3·ay" can be used

In accordance with an implementation option, the total acceleration threshold value atot_thr (in modulus) belongs to the range between 2 g and 5 g.

According to an embodiment, the accelerations of both detection points of the master device are calculated.

According to different possible implementation options of such an embodiment, the alarm trigger condition is raised if at least one of the aforesaid detected points exceeds the threshold acceleration, or if the virtual midpoint exceeds the threshold acceleration, or if the relative acceleration between the aforesaid two points is above threshold.

According to an implementation option, the aforesaid total acceleration threshold atot_thr is defined so as to increase with the decrease of the scale factor of the motion between the master device and the slave device, and/or with the decrease of a scale factor selected by the user and applied to the teleoperated Master-Slave movement.

According to an application example, in the field of robotic micro-surgery, the scale factor can be defined in a range between 5× and 20×. Obviously, the greater such a scale factor (for example, the slave movement is scaled 20 times), the greater the trigger threshold so as to allow accelerated movements.

For example, atot_thr1 is the threshold chosen for a scale factor S1, and T is the time taken by the system to recognize the acceleration and therefore to interrupt the teleoperation. In such a case, a maximum uncontrolled movement of the slave equal to $D=\frac{1}{2}$ S1 atot_thr1 $T^2$ is accepted. Then for the scale factor S2, setting the same distance traveled D and time T, atot_thr2=atot_thr1 S1/S2.

It should be noted that in a typical implementation option, the scale factor can be set by the user depending on the specific circumstances, and can be varied, reset by the user even during the movement of the slave.

In accordance with a method embodiment, in which the master device consists of two rigid parts mutually connected in an elastic joint which tends to open such parts at least angularly when not pressed or held firmly in the user's hand, the detectable anomaly/fault is an involuntary opening of the master device. Such a situation can occur, in particular, if the surgeon loses control, for example because the master device has escaped his hands, and the master device, dropping, opens by snapping due to the spring of the joint.

In such a case, the method comprises the following steps:

detecting and/or calculating the acceleration vector (as previously disclosed) and/or the respective evolution over time of each of said two detectable points;

calculating the opening angular acceleration ω of the two rigid parts of the master device, based on the aforesaid detected and/or calculated acceleration vectors;

comparing the calculated opening angular acceleration ω with a threshold angular velocity ω_thr which depends on the elastic rigidity of the elastic joint;

identifying the anomaly/fault condition associated with an involuntary opening of the master device if the aforesaid calculated opening angular acceleration ω is greater than the aforesaid threshold angular acceleration (ω_thr), according to the relation ω>ω_thr.

In accordance with an implementation option, the threshold angular acceleration value ω_thr depends on the elastic rigidity of the spring associated with the elastic joint and decreases with the increasing degree of opening between the rigid parts.

According to other implementation options, the aforesaid steps of calculating, comparing and identifying are performed not on the angular acceleration, but on the angular velocity, or on the linear velocity.

For example, according to another implementation option, again referring to the case in which the master device consists of two rigid parts mutually connected in an elastic joint which tends to open such parts at least angularly when not pressed or held firmly in the user's hand, and the detectable anomaly/fault is an involuntary opening of the master device, the method comprises the following steps:

detecting the position vector and the respective evolution over time of each of the two detectable points;

calculating the evolution over time of the distance between the aforesaid two detectable points, based on the evolution over time of the position vectors detected;

calculating the linear opening velocity v of the master device, based on the evolution over time of the aforesaid distance;

comparing the calculated opening linear velocity v with a threshold linear velocity v_thr;

identifying the aforesaid anomaly condition if v>v_thr.

In accordance with a method embodiment, in which the master device has two rigid parts elastically constrained to translate along a longitudinal axis coinciding with the longitudinal extension of at least one of the aforesaid parts of the master device, the method comprises the following steps:

detecting and/or calculating the acceleration vector and/or the respective evolution over time of each of the two detectable points;

calculating the distancing/approaching linear acceleration of the two rigid parts of the master device, based on the aforesaid detected and/or calculated acceleration vectors;

comparing the calculated distancing/approaching linear acceleration with a threshold linear acceleration which depends on the elastic rigidity of the constraint;

identifying the anomaly/fault condition associated with an involuntary opening of the master device if the calculated distancing/approaching linear acceleration is greater than the threshold linear acceleration.

In accordance with a method embodiment, the aforesaid anomalies of involuntary drop of the master device, excessive acceleration of the master device and sudden and/or involuntary opening of the master device are all detected, and at the same time.

Such an embodiment allows a wide spectrum of controls to be obtained, aiming at the maximum possible safety.

According to a preferred implementation option, the detection of the aforesaid anomalies of involuntary drop of the master device, excessive acceleration of the master device and sudden and/or involuntary opening of the master device are subject to the further constraint that the master device is within a predeterminable working volume assigned to the master device. Such a working volume can be defined so that it is positioned around the position taken by the surgeon during the teleoperation.

According to an embodiment, the method comprises the further step of detecting the position of at least one point belonging to or integral with the master device. In such a case, the further anomaly/fault associated with the detection of the master device positioning outside permitted limits can be detected through a comparison of the detected position of at least one point belonging to or integral with the master device with respect to a limit surface, in the absolute reference frame X, Y, Z.

Such a limit surface is, in several possible implementation options, a ball or a box (parallelepiped), or in general a polytope or the convex intersection of half-spaces.

A method for managing anomalies/faults identified in a master device of a master-slave robotic system for surgical or medical teleoperation is also comprised in the present invention.

Such a method includes performing a method for identifying and recognizing and/or discriminating at least one anomaly/fault condition according to any of the embodiments described above.

Such a method further includes, if at least any of the aforesaid anomalies/faults are determined, the step of immediately interrupting the teleoperation and the movements of the surgical instrument (or "end-effector") of the slave device, to safeguard the patient's safety.

A robotic system for medical or surgical teleoperation comprising at least one master device, at least one slave device and a control unit is further comprised in the present invention.

The at least one master device is mechanically ungrounded and adapted to be held in hand by a surgeon during surgery, and is configured to detect a manual command of the surgeon and generate a respective first electrical command signal.

The at least one slave device, or slave robotic assembly, comprises at least one slave surgical instrument configured to operate on the anatomy of a patient, in a controlled manner by the respective at least one master device.

The control unit provided with a computer is configured to receive the aforesaid first electrical command signal from the master device, generate a second electrical command signal, based on the first electrical command signal, and provide the second electrical command signal to the slave robotic assembly, to actuate the at least one slave surgical instrument.

The control unit is further configured to perform a method for identifying and recognizing and/or discriminating at least one anomaly/fault condition according to any of the previously disclosed embodiments.

According to an implementation option, the control unit is further configured to perform a method for managing identified anomalies/faults, according to any one of the previously described embodiments of the method for managing anomalies/faults.

In an implementation option of the system, the master device body comprises seats for receiving the one or more sensors in respective predeterminable positions.

According to a system embodiment, the master device body is disposable and thus typically made of plastic.

According to another system embodiment, the master device body is made of metal (e.g., titanium) and is sterilizable.

With reference to FIGS. 1-8, some embodiments of the method, previously defined in more general terms, will be further detailed below, by way of non-limiting example.

The anomaly checks of the master device are introduced into the robotic system for teleoperation in order to intervene with the minimum latency with respect to the actual movement.

In an embodiment, the sequence of operating actions carried out includes an acquisition of information on all the degrees of freedom of movement of the master device, for example in terms of acceleration; then, filtering the signals obtained; evaluating one or more anomaly checks on the master; detecting any faults or anomalies of the master device, based on the checks that are carried out; communicating with the control unit of the machine state of the robotic system, with the user interface UI and with the end points of the slave device.

Further details on the anomaly checks carried out in some embodiments of the method (already mentioned above) will be provided below, by way of non-limiting example.

Drop of the Master Device ("Master Drop").

The objective of this check is to identify an involuntary drop of the master device from the surgeon's hands. Such a check is based on the detection of acceleration (or position) of the master device (without the need for further sensors to detect other quantities, such as pressure-sensitive surfaces).

The principle consists in detecting the acceleration, or in deriving the acceleration from position information (even affected by noise) and calculating the instantaneous value of the acceleration along the (downwards) direction of the gravity vector.

When such an acceleration reaches a threshold which is comparable to the gravity acceleration, the anomaly warning is issued with respect to this check.

It is assumed in the following that, in the Global Reference System, the gravitational field is oriented along the −Y axis.

For example, the acceleration estimation is based on the use of a polynomial fitting of the Y axis, and then the double derivation of the polynomial by manipulating the coefficients thereof.

Among the different fitting techniques that can be used, it is possible to mention, for example, the solution based on the Solezky-Golay filter, which is characterized in that it expresses the polynomial derived as in the FIR (Finite Impulse Response) filter, which operatively consists of taking a window of 2W+1 samples and multiplying it by a constant matrix. Such a matrix depends on two parameters: the size of the window (with half-width W) and the order of the polynomial.

The size of the window depends on the sampling time, the desired latency in computation, and the signal noise.

The order of the polynomial depends on the nature of the positional signal.

The filter is a low-pass filter, with cutoff frequency which can be expressed according to relations known in the literature, for example:

$$\text{Cutoff (Hz)}=Dt(\text{Order}+1)/(3.2\ \text{Window}-4.6).$$

According to an implementation option, the master device has two detection positions (i.e., two sensors). In such a case, when any one thereof exceeds the threshold, an anomaly warning is issued.

It should be noted that the wider the window used for the estimate, the better the estimate itself, with the aforesaid algorithm. On the other hand, the narrower the window, the faster the reaction time.

A criterion for choosing an appropriate compromise between the aforesaid needs is the amount of space traveled by the controlled slave device during the unintuitive and undesired movement of the master device (for example, the dropping movement of the master). The maximum distance allowed to the path by the controlled slave device during the non-intuitive movement defined as D, and the maximum velocity of the master in this situation defined as M, then the maximum window width W is expressed by the relation:

$$W=2D/M/T+1,$$

where T is the sampling time.

Exceeding a Maximum Acceleration

Another type of anomaly check is related to an unintuitive movement is an excess acceleration of the master device along any direction. This event can be identified based on a detection or estimation of acceleration component by component, using the same techniques described above for the "Master Drop" case.

In this case, the vector modulus of the three components is compared with a threshold to issue any anomaly warning.

Sudden Opening of the Master Device.

In the case of a master device having a degree of freedom related to grip, a further check can be carried out on a possible sudden opening (i.e., excessively fast with respect to what can be expected in normal conditions of voluntary control by the operator) of the grip of the master device, which is considered indicative of an involuntary opening, i.e., for example, of the abnormal situation in which the operator loses control of the master device, or of the grip on the master device, where the degree of freedom of grip of the master device is elastically preloaded at opening or closing.

The estimation of the opening velocity is performed, for example, using the same polynomial fitting described above for the "Master Drop" case, but with different parameters, associated with this particular condition.

The estimated velocity of the opening angle (or "grip angle") obtained from the fitting is used for the evaluation of this anomaly.

In one case, the opening acceleration is estimated: the estimation of the opening acceleration is performed, for example, using the same polynomial fitting described above for the "Master Drop" case, but with different parameters, associated with this particular condition. The opening acceleration depends on the preload elasticity (for example, a spring can be included between two rigid parts constrained to rotate). The estimated acceleration of the opening angle (or "grip angle") obtained from the fitting is used for the evaluation of this anomaly.

Master Device Outside Spatial Limits.

Another anomaly check is related to the spatial limits prescribed for operator movement. These limits are defined based on usability considerations of the specific surgical target and limitations of the sensor system used to calculate the position of the master device.

Two main scenarios can be identified in relation to such limits: a sphere centered in the center of the workspace; or a parallelepiped-shaped surface; or a geometry in which it is computationally efficient to calculate whether a point is therein or not.

When the limits of such volumes are reached by the master device, an anomaly notification is provided to the user.

In the context of a master device with constrained mechanical interface, these limits depend on the limits of the mechanical interface.

In the context of a master device with an unconstrained (ungrounded) mechanical interface, if an optical detection is considered, the workspace is the intersection of the cone trunks of each camera, built taking into account the minimum resolution necessary to identify the features being tracked. When considering magnetic tracking systems, the workspace has limits which depend on the attenuation of the magnetic field.

Thus, in summary, according to a method embodiment, by measuring or calculating the vector acceleration, i.e., modulus and direction, linear acceleration or angular acceleration of the master device, at least the following information is obtained:

- master device drop: if the acceleration is equal to g or around g (for example, 80% of g) and directed downwards, then the robotic system is immediately stopped, to prevent the slave from also heading downwards, and therefore, presumably, towards the patient;
- the master device has an excessive acceleration (e.g., equal to or greater than 3 g) in any direction; also in this case, the robotic system is immediately stopped;
- unintentional opening of the master device: if the relative acceleration of two points of the master device is greater than the elastic return acceleration between the aforesaid two points (between which there is a joint, and a spring adapted to open the joint).

The vector acceleration of the master device is either directly detected by one or more accelerometers, or derived from monitoring the evolution of the position vector, in turn detected.

As disclosed above, the present method relates to a broad class of master device interfaces for robotic systems of surgical teleoperation, characterized by position and orientation measurements.

In particular, master devices with two parts, or tips, which can be closed with a hinge or hinge joint are for example considered. Each part is associated with a position measurement, which is directly measured or deducted.

In such a case, the measurements performed on the two parts of the master device can provide up to 12 degrees of freedom detected: 3 position coordinates and 3 orientation values for the first master device portion; 3 position coordinates and 3 orientation values for the second master device portion.

Such detections always allow (and also with redundancy) to detect the 7 degrees of freedom of the mechanical structure of the master device.

The examples shown in FIGS. 1, 2, 7 and 8 refer to a "gripper" type master device which involves the application of a force of the fingers of the gripping hand about in the middle between the hinge joint and the tips of the two arms of the gripper (corresponding to the "two parts" of the master device mentioned several times). This type of master device is characterized by a total of 7 degrees of freedom: three orientation degrees of freedom, three position degrees of freedom and the opening between the gripper arms. As already described, optical or magnetic technologies can be used to detect the position of the gripper arms.

Figure 2:
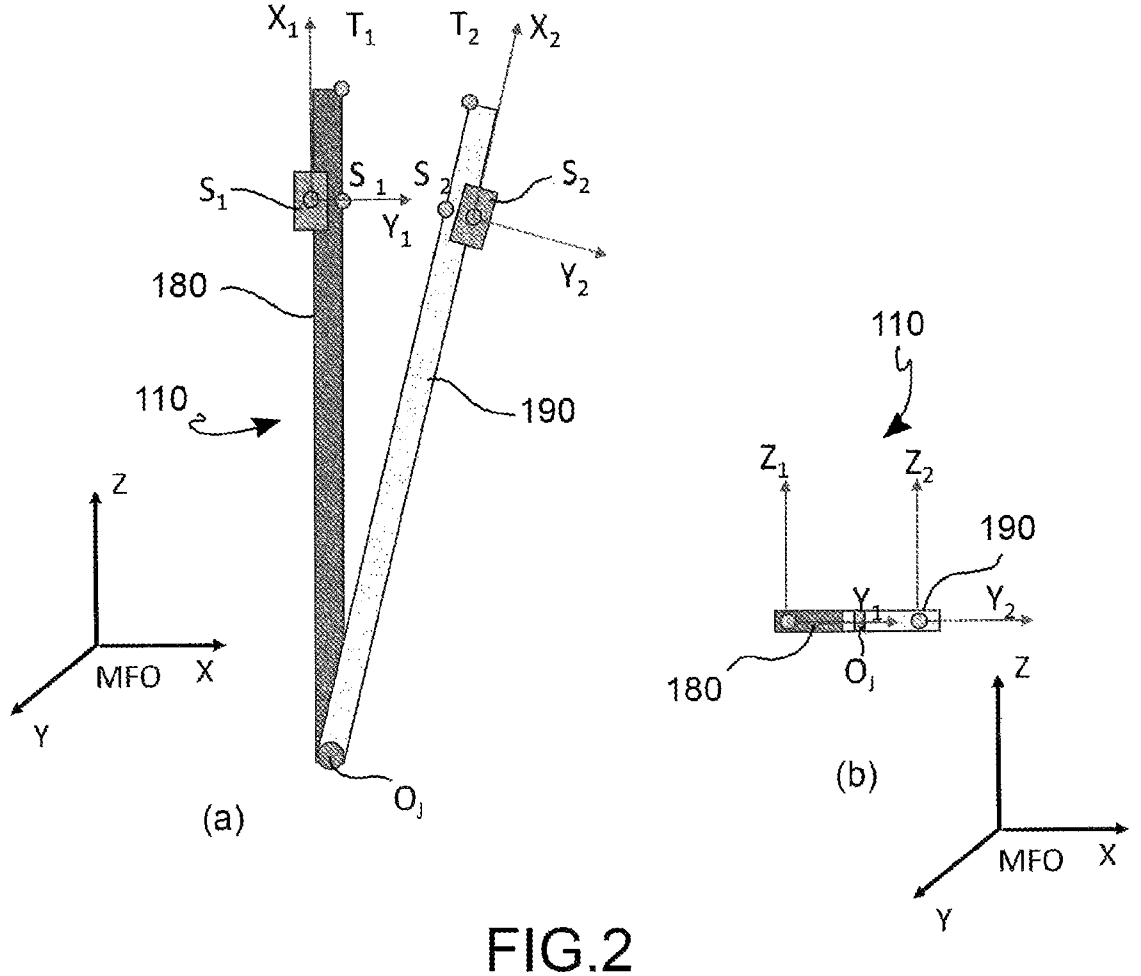

FIGS. 1 and 2 depict the master device with the two sensors S1, S2 arranged near the tips T1, T2 of the gripper arms.

In FIG. 1, the hinge joint OJ is on the left, and allows a rotation of the arms with an axis parallel to the two axes z1 and z2 of the two rigid arms or parts 180, 190. The axes x1 and x2 are in the direction of the arms, with a direction away from the joint.

The position and rotation measurements of each of the two sensors can be represented by a three-dimensional vector of the position (thus obtaining two position vectors which we indicate as p1 and p2) and by a rotation matrix for each arm (thus obtaining two rotation matrices which we indicate as R1 and R2). Each sensor is then associated with respective position and rotation information, (p1, R1) and (p2, R2).

It should be noted that the rotation can be associated with the three-dimensional orthogonal subgroup SO(3) and thus the number of degrees of freedom is always 3 (regardless of the type of representation, whether it is based on a rotation matrix with 9 numbers, as exemplified herein, or based on 3 Euler angles (3), or based on quaternions.

The arrangement (i.e., pose, i.e., position and rotation) of the reference points (or tips) of the arms allows calculating an arrangement (i.e., pose, i.e., position and rotation) of the entire master device, for example with a position calculated as the average pM of the two positions p1 and p2, and rotation as an average of the rotations (i.e., a matrix RM having as elements the averages of the respective elements of R1 and R2). The opening angle $\alpha$ of the gripper can be calculated using the distances between the tips and the known lengths of the master device arms, i.e., the known distances between the joint OJ and each of the reference points provided with sensors S1, S2 (assuming that the sensors are placed at equidistant points from the joint OJ, the aforesaid two distances are equal, and are referred to herein as D).

Figure 3:
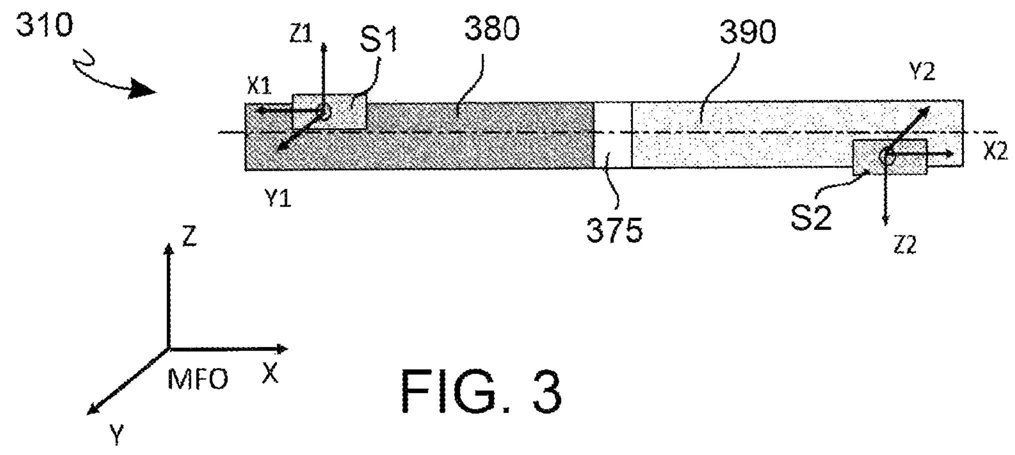
FIG. 3 shows geometric parameters and reference frames used in the method of the present invention, applied to an embodiment of the master device with a "pen" structure.

According to an implementation option, shown for example in FIG. 3, said master device 310 has two rigid parts 380, 390, preferably co-linear with each other, elastically constrained in a portion 375, for example a prismatic joint, to translate along a longitudinal axis coinciding with the longitudinal extension of at least one of, or both, of the aforesaid parts 380, 390 of the master device 310. For example, pressing radially on the portion 375 determines the relative distancing of the two parts 380, 390.

In such a case, as already observed, the method comprises: detecting and/or calculating the acceleration vector and/or the respective evolution over time of each of said two detectable points; calculating the relative linear acceleration of translation of the two rigid parts of the master device constrained to translate elastically, based on said detected and/or calculated acceleration vectors; comparing the calculated relative linear acceleration of translation with a threshold linear acceleration which depends on the elastic rigidity of the constraint; and finally identifying the anomaly condition if the calculated relative linear acceleration of translation is greater than the threshold linear acceleration.

The threshold linear acceleration can be an approaching acceleration threshold between the two rigid portions and/or a distancing acceleration threshold. For example, when in operating conditions, a radial pressure action on the master device body causes the two rigid parts to move away, imparting a gripping action (opening/closing) to the surgical slave instrument.

Preferably, this implementation option which provides calculating the relative linear acceleration of translation of the two rigid parts of the master device constrained to each other in translation allows identifying an indicative anomaly condition of an uncontrolled behavior of the master device, like the implementation described above with reference to the involuntary opening in a master device having a rotational joint between the two rigid parts.

Figure 4:
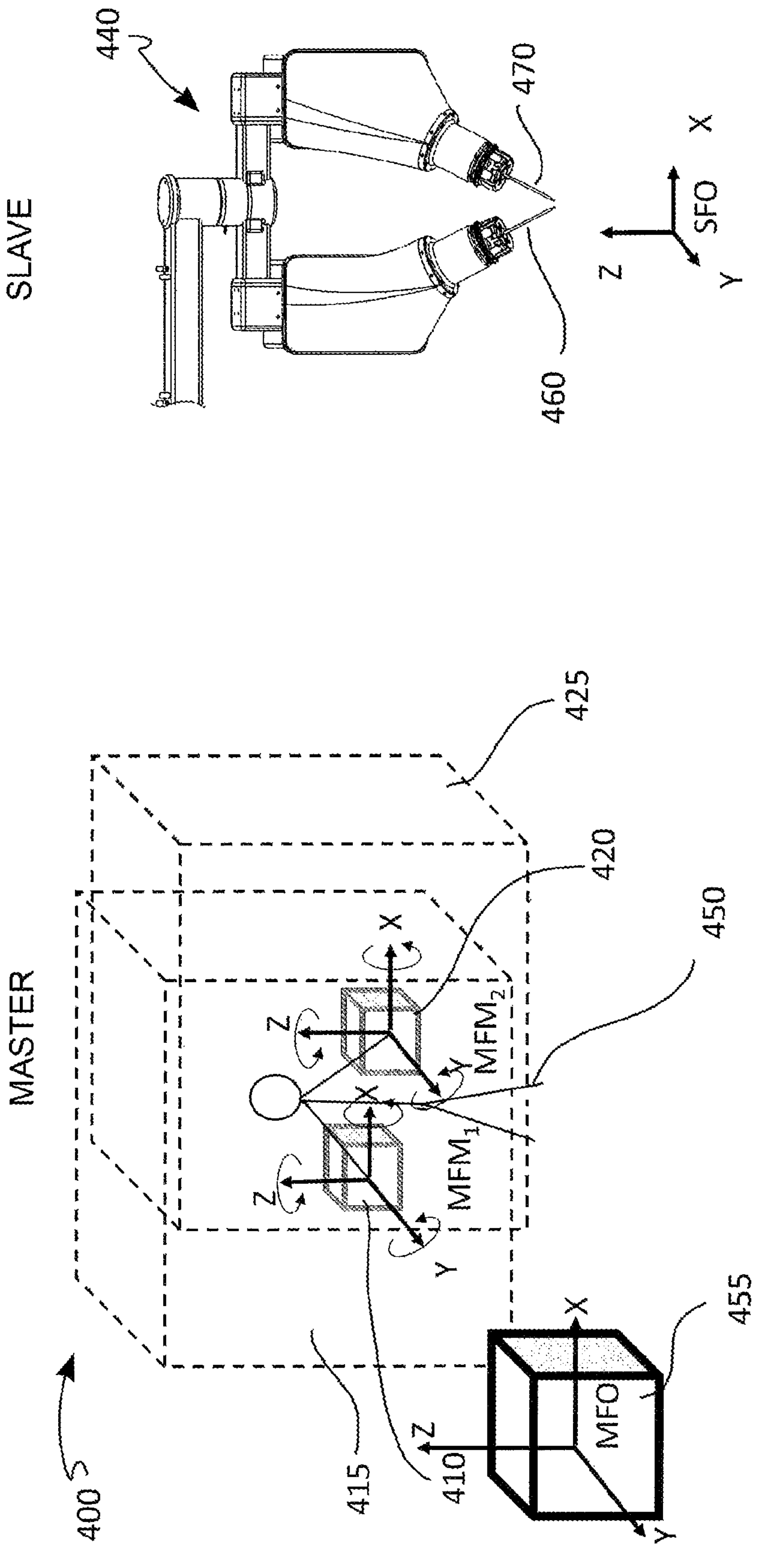

According to an embodiment shown in FIG. 4, a robotic teleoperated surgery system 400 comprises at least one unconstrained master device 410, 420 having an assigned workspace 415, 425 (in the illustrated example, two diagrammatically shown unconstrained master devices 410, 420 are diagrammatically shown held in hand by a surgeon 450), a console 455 being integral with the workspaces 415, 425, a control unit 430, and a slave device 440 (in the illustrated example, two slave surgical instruments 460, 470 are shown).

According to an embodiment shown in FIG. 4*bis*, a robotic teleoperated surgery system 400 comprises at least one unconstrained master device (in the illustrated example, two unconstrained master devices shown diagrammatically held in hand by a surgeon 450 within a workspace 415), a console 455, and a slave device 440 (in the illustrated example, two slave surgical instruments 460, 470 are shown), which console 455 defines a general reference frame MFO which is integral with the workspace 415, and in which each master device defines a local reference frame MFM1 and MFM2.

With respect to the coordinate frames shown in the figures and used in the method, it should be noted that the reference frame denoted as MFO is a general reference frame for the master device (e.g., associated with the workspace of the master device); the reference frames denoted as MF #1 and M2 (FIG. 1) are local reference frames which are integral with the two parts of the master device; the reference frames MFM (in FIG. 1), MFM1 and MFM2 (FIGS. 4 and 4*bis*) are local reference frames which are integral with a master device (e.g., associated with a virtual midpoint between the points where two sensors being integral with the master device are located); the reference frame SFO is a general reference frame for the slave device (e.g., associated with a workspace of the slave device).

According to an embodiment shown in FIG. 4*ter*, a master console 455 for a robotic teleoperated surgery system comprises a screen 457 and a tracking source 456 which is integral with a working volume 415; two unconstrained master devices 410, 420 are shown within the work volume 415, each unconstrained master device 410, 420 being wired via data link 411, 421 to the console 455.

FIGS. 5, 6, 7 and 8 show some anomalies which can be identified based on acceleration information of at least one point of the unconstrained master device.

Figure 5:
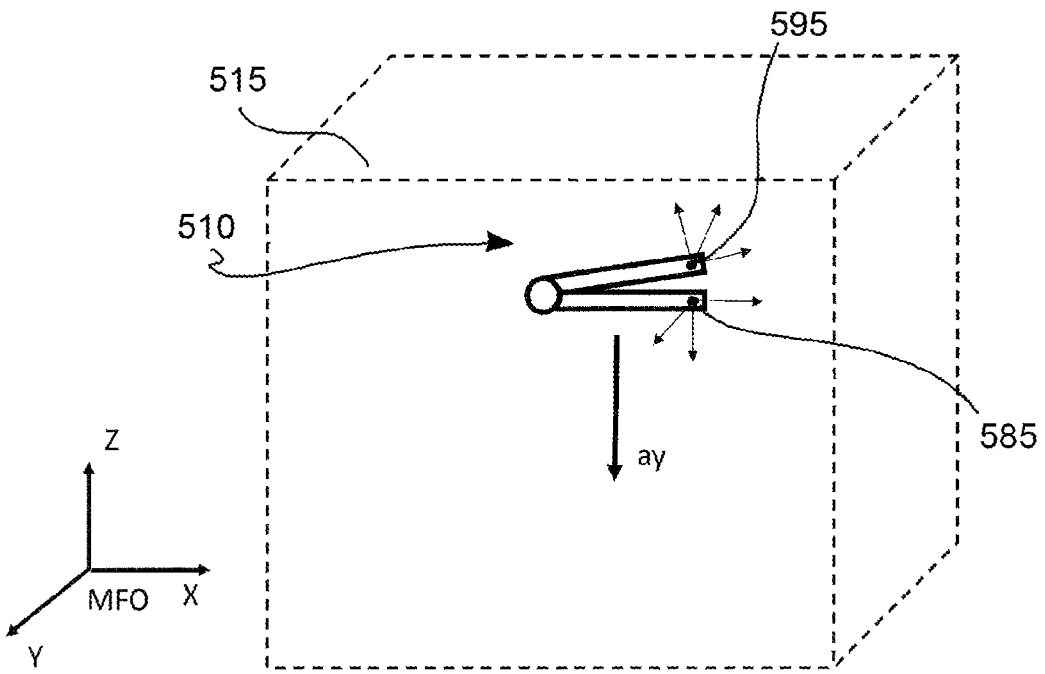
FIGS. 5-8 diagrammatically show some anomalies that are detectable by means of some embodiments of the method.

In particular, FIG. 5 shows an unconstrained (ungrounded) master device 510 within the workspace or working volume 515 assigned thereto and provided with two sensors 585, 595 or markers 585, 595, in which the master device 510 is shown subject to an above-threshold vertical acceleration ay.

Figure 6:
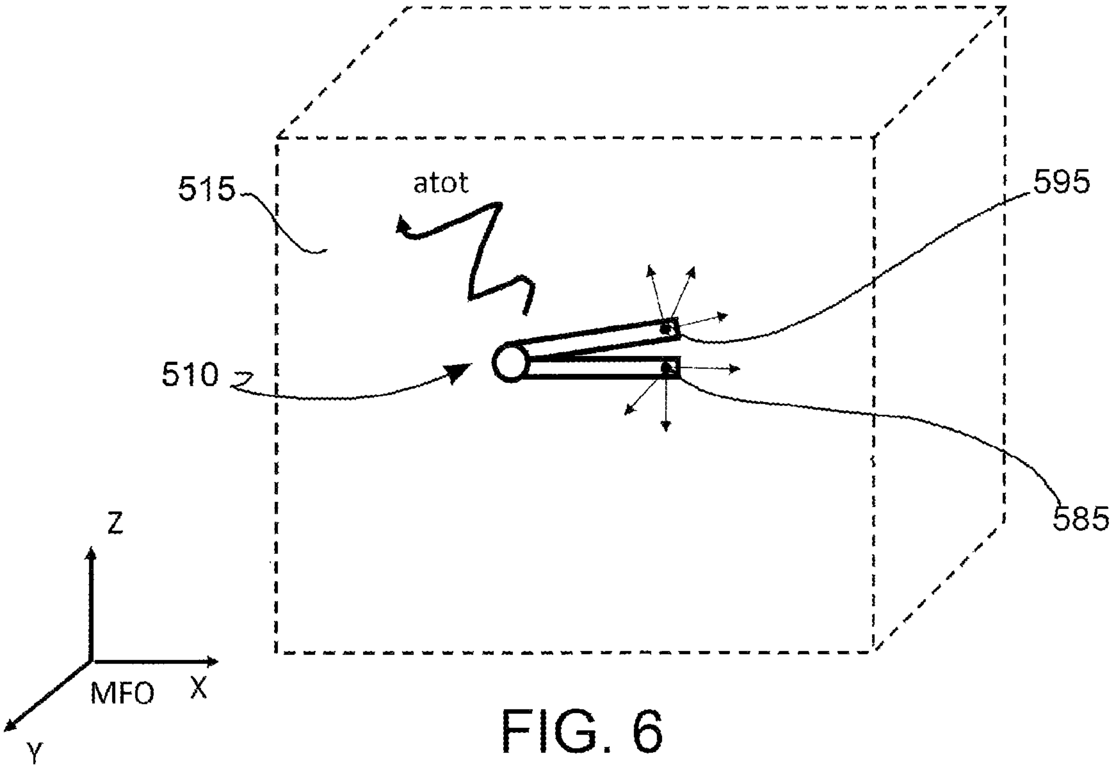

FIG. 6 shows an unconstrained (ungrounded) master device 510 within the workspace or working volume 515 assigned thereto and provided with two sensors 585, 595 or markers 585, 595 on respective parts 580, 590, in which the master device 510 is shown subject to an above-threshold acceleration atot.

Figure 7:
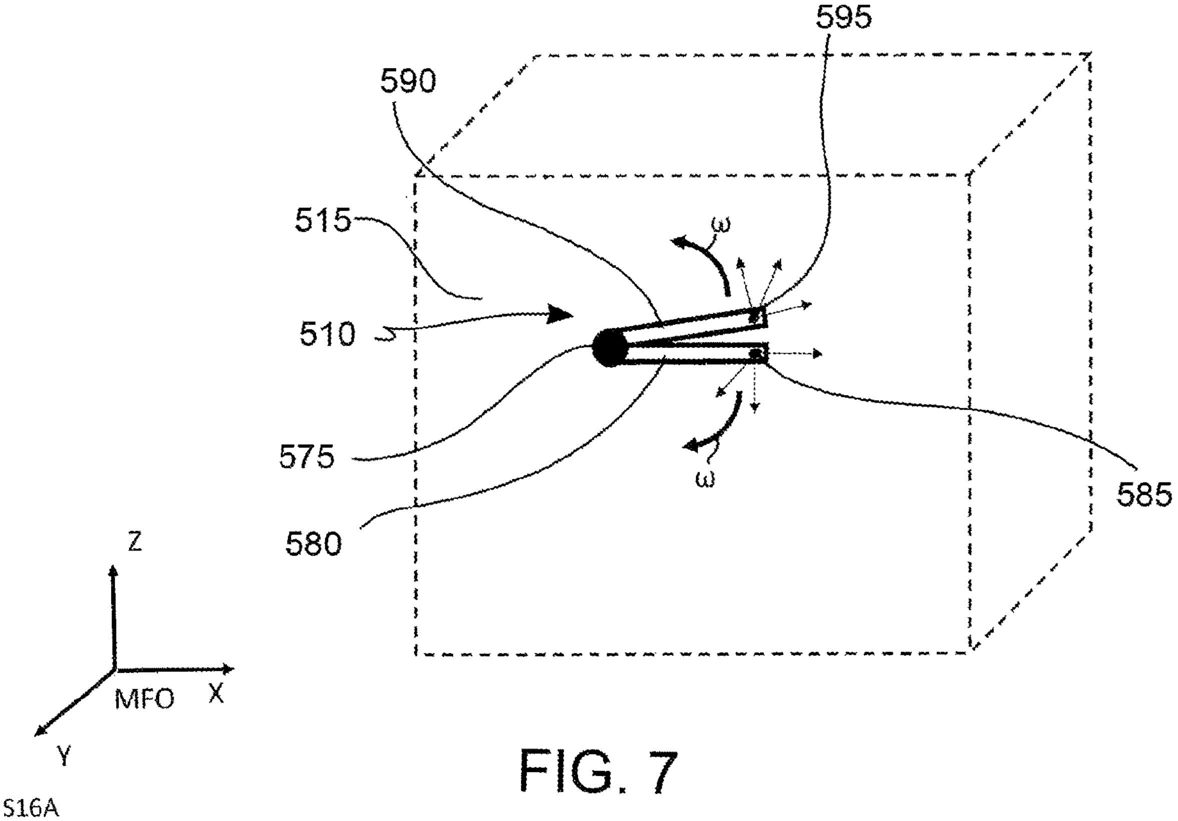

FIG. 7 shows an unconstrained (ungrounded) master device 510 within the workspace or working volume 515 assigned thereto, in which the body of the master device 510 is formed by two rigid parts 580, 590 constrained in an elastic joint 575 to relatively rotate about a common axis, in which each of said two rigid parts 580, 590 is provided with a sensor 585, 595 or marker 585, 595, in which the master device 510 is shown subject to involuntary opening (in this embodiment shown, the elastic joint 575 biases the free ends of the rigid parts 580, 590 to move away, with an angular acceleration ω which depends on the elasticity of the elastic joint 575). In place of (or in addition to) the detection of the angular acceleration w, the linear acceleration can be detected.

Figure 8:
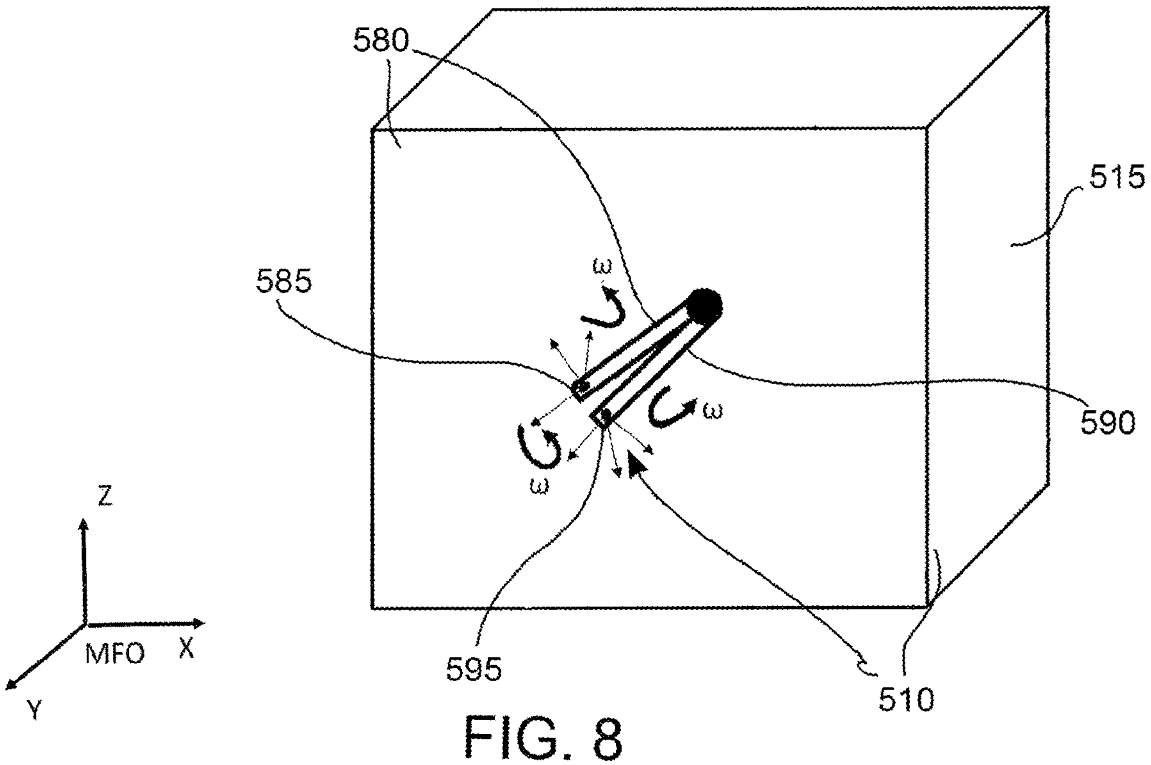

FIG. 8 shows an unconstrained (ungrounded) master device 510 within the workspace or working volume 515 assigned thereto and provided with two sensors 585, 595 or markers 585, 595 on respective parts 580, 590, in which the master device 510 is shown subject to an angular acceleration ω on each of the axes of the general reference frame MFO.

A robotic system 400 for medical or surgical teleoperation comprising a master device, at least one slave device and a control unit is described below.

The master device (110; 310; 410, 420; 510) is mechanically ungrounded and adapted to be held in hand by a surgeon 450 during surgery, and configured to detect a manual command of the surgeon and generate a respective first electrical command signal. The at least one slave device 440, or slave robotic assembly, comprises at least one slave surgical instrument 460, 470 configured to operate on the anatomy of a patient, in a manner controlled by the master device.

The control unit provided with a computer is configured to receive said first electrical command signal from the master device, generate a second electrical command signal, based on the first electrical command signal, and provide the second electrical command signal to the slave robotic assembly, to actuate the at least one slave surgical instrument.

The control unit is configured to identify and recognize and/or discriminate at least one anomaly/fault condition, among a detectable set of anomalies/faults comprising at least one of the following: involuntary drop of the master device and/or excessive acceleration of the master device and/or sudden and/or involuntary opening of the master device.

Each of such detectable anomalies/faults is associated with at least one system state change to be performed if the anomaly is detected.

To identify and recognize and/or discriminate at least one anomaly/fault condition, the control unit is configured to perform the following actions:

- detecting and/or calculating, based on information sent by one or more sensors (S1, S2), (585, 595) of the robotic system operatively connected to the control unit, the acceleration vector of at least one point belonging to or integral with the master device, or of a virtual point uniquely and rigidly associated with the master device;
- identifying and recognizing and/or discriminating at least one detectable anomaly/fault condition based on at least one component or modulus of said detected and/or calculated acceleration vector.

According to an embodiment of the robotic system, the aforesaid master device consists of two rigid parts 580, 590 mutually connected in an elastic joint which tends to open such parts at least angularly when not pressed or held firmly in hand by the user.

The anomaly to be detected is an involuntary opening of the master device, and the control unit is configured to: detect and/or calculate the acceleration vector and/or the respective evolution over time of each of two detectable points; calculate the opening angular acceleration ω of the two rigid parts of the master device, based on the aforesaid detected and/or calculated acceleration vectors; compare the calculated opening angular acceleration ω with a respective threshold angular acceleration which depends on the elastic rigidity of the elastic joint; identify the anomaly condition associated with an involuntary opening of the master device if the aforesaid calculated opening angular acceleration ω is greater than said threshold angular acceleration, according to the relation ω>threshold angular acceleration.

According to an embodiment of the robotic system, the aforesaid master device comprises two rigid parts 380, 390 elastically constrained to translate along a longitudinal axis coinciding with the longitudinal extension of at least one of the aforesaid parts of the master device.

The control unit is configured to detect and/or calculate the acceleration vector and/or the respective evolution over time of each of said two detectable points; calculate the distancing/approaching linear acceleration of the two rigid parts of the master device, based on the aforesaid detected and/or calculated acceleration vectors; compare the calculated distancing/approaching linear acceleration with a threshold linear velocity which depends on the elastic rigidity of the constraint 375; identify the anomaly/fault condition associated with an involuntary opening of the master device if the aforesaid calculated distancing/approaching linear acceleration is greater than the aforesaid threshold linear acceleration.

According to an embodiment of the robotic system, the aforesaid master device comprises two rigid parts 580, 590 mutually connected in an elastic joint which tends to open said parts at least angularly when not pressed or held firmly in the user's hand.

The anomaly to be detected is a drop of the master device, and the control unit is configured to detect the drop of the master device based on the relation between the accelerations of two sensors respectively associated with the aforesaid two rigid parts of the master device.

According to different embodiments of the robotic system, the control unit is configured to identify and recognize and/or discriminate at least one anomaly condition by performing a method according to any of the embodiments of such a method disclosed in this description.

According to an embodiment of the robotic system, the control unit is configured to manage anomalies found by performing a method according to any of the embodiments of such a method disclosed in this description.

As can be seen, the objects of the present invention as previously indicated are fully achieved by the method described above by virtue of the features disclosed above in detail.

In fact, the method and system described allow an effective and real-time verification of detecting several possible operating anomalies/faults of the master device, or possible abnormal situation of the master device, and recognizing the type of anomaly.

Thus, the need to apply procedures for verifying any abnormal operating conditions of the master device in real time, conducted automatically by the robot control system for medical or surgical teleoperation, such as to be efficient and reliable, in order to meet the stringent safety requirements which are required by such applications, are met.

This is achieved by measuring or calculating the linear and/or angular acceleration of at least one point which can be associated with the master, preferably when the unconstrained or "flying" master device is within a certain working volume, and comparing the one or more detected quantities with one or more respective predeterminable threshold values.

Since the master device is intended to be mechanically hand-held by the surgeon during teleoperation, the detection of accelerations of the master device outside permitted limits when the master device is within the workspace assigned to the master is an indication of anomaly.

Once a structural or functional anomaly of the master device has been identified, the teleoperation can be immediately and promptly interrupted, thus avoiding that such an anomaly is reflected in a consequent anomaly in the operation of the slave device and the surgical instrument associated therewith, intended to act on the patient, with possible even serious consequences on the patient himself.

Thereby, the objective of improving patient safety is achieved, meeting the very strict safety requirements which must be respected in the operating environment considered.

In order to meet contingent needs, those skilled in the art may make changes and adaptations to the embodiments of the method described above or can replace elements with others which are functionally equivalent, without departing from the scope of the following claims. All the features described above as belonging to a possible embodiment may be implemented irrespective of the other embodiments described.

The invention claimed is:

1. A method for identifying and recognizing and/or discriminating at least one anomaly condition in using a master device, which is hand-held, to be held in hand by an operator, and mechanically ungrounded, to control a robotic system for medical or surgical teleoperation, wherein the method comprises:

detecting and/or calculating, by one or more sensors, an acceleration vector of at least one point belonging to or integral with the master device, or of a virtual point uniquely and rigidly associated with the master device;

identifying and recognizing and/or discriminating at least one detectable anomaly condition based on at least one component or modulus of said detected and/or calculated acceleration vector;

wherein said detectable anomalies comprise at least one of the following: involuntary drop of the master device and/or excessive acceleration of the master device and/or sudden and/or involuntary opening of the master device, wherein said excessive acceleration is an acceleration larger than a predefined acceleration threshold, wherein said sudden opening of the master device is an opening of the master device faster than what expected in conditions of voluntary control by the operator, wherein each of said detectable anomalies is associated with at least one system state change to be performed if the anomaly is detected, wherein the anomaly to be detected is said excessive acceleration of the master device, imparted in the movement by said user, and wherein the method comprises:

detecting and/or calculating an acceleration vector modulus (atot) of at least one of said at least two detected points;

comparing the detected and/or calculated acceleration vector modulus (atot) with a total acceleration threshold;

identifying the anomaly associated with said excessive acceleration of the master device if said acceleration vector modulus (atot) is greater than said total acceleration threshold, according to the relation: atot>total acceleration threshold.

2. A method according to claim 1, wherein said system state change, to be performed if an anomaly is detected, comprises exiting the teleoperation.

3. A method according to claim 1, comprising the further step of measuring and/or detecting, by one or more sensors, a position vector of said at least one point belonging to or integral with the master device and of evolution over time of said position vector;

and wherein the step of detecting and/or calculating said acceleration vector comprises detecting and/or calculating said acceleration vector based on evolution over time of the respective measured and/or detected position vector.

4. A method according to claim 3, wherein said step of detecting and calculating the acceleration vector comprises:

calculating the acceleration vector by movable windows of N samples of the vector representing the position vector evolution over time, and by interpolation with second order polynomials, for a degree of freedom related to grip, and with third order polynomials, for the degrees of freedom related to the master device translation and orientation, or calculating the acceleration vector by a Kalman-type predictive filter which uses a movement model with random acceleration dynamics adapted to estimate a master device position state and correct an estimate based on information provided by a measurement system.

5. A method according to claim 1, wherein said step of detecting and/or calculating the acceleration vector comprises:

detecting and/or calculating the acceleration vector of each of at least two points belonging to or integral with the master device by at least two sensors;

calculating the acceleration vector of a virtual point uniquely and rigidly associated with the master device, corresponding to a midpoint between the points where the sensors are located.

6. A method according to claim 1, wherein said measuring and/or detecting step is performed with respect to a reference coordinate frame associated with the robotic system for teleoperated surgery, and having predetermined axes and origin in a predetermined point.

7. A method according to claim 6, wherein the robotic system for medical or surgical teleoperation comprises an operating console, wherein said reference coordinate frame is integral with said robotic system console, and/or wherein the robotic system for medical or surgical teleoperation comprises a tracking system, for detecting an input position and orientation of the master device within a predetermined tracking volume, wherein actuation of the slave surgical instrument depends on a manual command given by the surgeon by the master device and/or on the position and orientation of the master device.

8. A method according to claim 1, wherein the master device is a hand-held and groundless master device, comprising two rigid parts constrained to relatively rotate and/or translate with respect to a common axis, wherein said detecting and/or calculating step comprises detecting and/or calculating, by respective sensors, the acceleration vector and/or the acceleration vector evolution over time, of at least two detectable points, a first point belonging to or integral with one of said rigid parts of the master device and a second point belonging to or integral with the other one of said rigid parts of the device, and/or wherein said calculating step comprises calculating the acceleration vector and/or the velocity vector of said at least two detectable points, or calculating the acceleration vector and/or the velocity vector of one of said at least two detected points, and further calculating the acceleration vector and/or the velocity vector and/or the position vector of at least one of the following further points:

midpoint between said two detected points and/or the center of gravity of the master device, and/or a rotational joint of the master device, and/or a prismatic joint of the master device.

9. A method for identifying and recognizing and/or discriminating at least one anomaly condition in using a master device, which is hand-held, to be held in hand by an operator, and mechanically ungrounded, to control a robotic system for medical or surgical teleoperation, wherein the method comprises:

detecting and/or calculating, by one or more sensors, an acceleration vector of at least one point belonging to or integral with the master device, or of a virtual point uniquely and rigidly associated with the master device;

identifying and recognizing and/or discriminating at least one detectable anomaly condition based on at least one component or modulus of said detected and/or calculated acceleration vector;

wherein said detectable anomalies comprise at least one of the following: involuntary drop of the master device and/or excessive acceleration of the master device and/or sudden and/or involuntary opening of the master device, wherein said excessive acceleration is an acceleration larger than a predefined acceleration threshold, wherein said sudden opening of the master device is an opening of the master device faster than what expected in conditions of voluntary control by the operator;

wherein each of said detectable anomalies is associated with at least one system state change to be performed if the anomaly is detected;

wherein the anomaly to be detected is said involuntary drop of the master device, and wherein the method comprises:

detecting and/or calculating a vertical acceleration component (ay), parallel to the gravity axis, of said at least one detected point;

comparing the detected or calculated vertical acceleration component (ay) with a vertical acceleration threshold;

identifying the anomaly associated with the involuntary drop of the master device if said vertical acceleration component (ay) is greater than said vertical acceleration threshold, according to the relation: ay>vertical acceleration threshold.

10. A method according to claim 9, wherein the acceleration vector of each of said at least two detection points of the master device is calculated to provide redundancy and/or a further verification.

11. A method according to claim 9, wherein the accelerations of both of said detection points of the master device are calculated, and wherein an alarm trigger condition is raised if at least one of said detected points exceeds the threshold acceleration, or if a virtual midpoint exceeds the threshold acceleration, or if relative acceleration between said two points exceeds the threshold.

12. A method according to claim 1, wherein said total acceleration threshold is defined to increase with a decrease of a scale factor of the motion between the master device and the slave device, and/or with a decrease of a scale factor selected by the user and applied to teleoperated Master-Slave movement.

13. A method according to claim 1, wherein said master device comprises two rigid parts mutually connected in an elastic joint which tends to open said parts at least angularly when not pressed or held firmly in hand by the user, and the anomaly to be detected is an involuntary opening of the master device, and wherein the method comprises:

detecting and/or calculating the acceleration vector and/or the respective evolution over time of each of said two detectable points;

calculating opening angular acceleration (ω) of the two rigid parts of the master device, based on said detected and/or calculated acceleration vectors;

comparing the calculated opening angular acceleration (ω) with a respective threshold angular acceleration which depends on elastic rigidity of the elastic joint;

identifying the anomaly condition associated with an involuntary opening of the master device if the calculated opening angular acceleration (ω) is greater than said threshold angular acceleration, according to the relation ω>threshold angular acceleration.

14. A method according to claim 1, wherein said master device comprises two rigid parts elastically constrained to translate along a longitudinal axis coinciding with the longitudinal extension of at least one of the parts of the master device, and wherein the method comprises:

detecting and/or calculating the acceleration vector and/or the respective evolution over time of each of said two detectable points;

calculating distancing/approaching linear acceleration of the two rigid parts of the master device, based on said detected and/or calculated acceleration vectors;

comparing the calculated distancing/approaching linear acceleration with a threshold linear velocity which depends on elastic rigidity of the constraint;

identifying an anomaly condition associated with an involuntary opening of the master device if said calculated distancing/approaching linear acceleration is greater than said threshold linear acceleration.

15. A method according to claim 1, wherein said anomalies of involuntary drop of the master device, excessive acceleration of the master device, and sudden and/or involuntary opening of the master device are all detected, and at the same time; and/or wherein the detection of said anomalies of involuntary drop of the master device, excessive acceleration of the master device, and sudden and/or involuntary opening of the master device are subject to a further constraint that the unconstrained master device is within a predeterminable working volume.

16. A method for managing anomalies identified in a master device of a master-slave robotic system for surgical or medical teleoperation, comprising the steps of:

performing a method for identifying and recognizing and/or discriminating at least one anomaly condition according to claim 1;

if at least any one of said anomalies is determined, immediately stopping the teleoperation and the movements of the surgical instrument of the slave device.

17. A robotic system for medical or surgical teleoperation comprising:

a master device, mechanically ungrounded and adapted to be held in hand by a surgeon during surgery, and configured to detect a manual command of the surgeon and generate a respective first electrical command signal;

at least one slave device, or slave robotic assembly, comprising at least one slave surgical instrument configured to operate on a patient, in a manner controlled by the master device;

a control unit provided with a computer, configured to receive said first electrical command signal from the master device, generate a second electrical command signal, based on the first electrical command signal, and provide the second electrical command signal to the slave robotic assembly, to actuate the at least one slave surgical instrument;

wherein said control unit is configured to identify and recognize and/or discriminate at least one anomaly condition, by carrying out the following actions:

detecting and/or calculating, based on information sent by one or more sensors of the robotic system operatively connected to the control unit, an acceleration vector of at least one point belonging to or integral with the master device, or of a virtual point uniquely and rigidly associated with the master device;

identifying and recognizing and/or discriminating at least one detectable anomaly condition based on at least one component or modulus of said detected and/or calculated acceleration vector;

wherein said detectable anomalies comprise at least one of the following: involuntary drop of the master device and/or excessive acceleration of the master device and/or sudden and/or involuntary opening of the master device, wherein said excessive acceleration is an acceleration larger than a predefined acceleration threshold, wherein said sudden opening of the master device is an opening of the master device faster than what expected in conditions of voluntary control by the operator;

wherein each of said detectable anomalies is associated with at least one system state change to be performed if the anomaly is detected; and wherein the anomaly to be detected is said excessive acceleration of the master device; and wherein the control unit is configured to:

detect and/or calculate an acceleration vector modulus (atot) of at least one of said at least two detected points;

compare the detected and/or calculated acceleration vector modulus (atot) with a total acceleration threshold;

identify the anomaly associated with said excessive acceleration of the master device if said acceleration vector modulus (atot) is greater than said total acceleration threshold, according to the relation: atot>total acceleration threshold.

18. A robotic system according to claim 17, wherein said master device comprises two rigid parts mutually connected in an elastic joint which tends to open said parts at least angularly when not pressed or held firmly in hand by the user, and the anomaly to be detected is an involuntary opening of the master device, and wherein the control unit is configured to:

detect and/or calculate the acceleration vector and/or the respective evolution over time of each of said two detectable points;

calculate opening angular acceleration (ω) of the two rigid parts of the master device, based on said detected and/or calculated acceleration vectors;

compare the calculated opening angular acceleration (ω) with a respective threshold angular acceleration which depends on elastic rigidity of the elastic joint;

identifying the anomaly condition associated with an involuntary opening of the master device if the calculated opening angular acceleration (ω) is greater than said threshold angular acceleration, according to the relation ω>threshold angular acceleration.

19. A robotic system according to claim 17, wherein said master device comprises two rigid parts elastically constrained to translate along a longitudinal axis coinciding with a longitudinal extension of at least one of the parts of the master device, and wherein the control unit is configured to:

detect and/or calculate the acceleration vector and/or the respective evolution over time of each of said two detectable points;

calculate the distancing/approaching linear acceleration of the two rigid parts of the master device, based on said detected and/or calculated acceleration vectors;

compare calculated distancing/approaching linear acceleration with a threshold linear velocity which depends on elastic rigidity of the constraint;

identify the anomaly condition associated with an involuntary opening of the master device if said calculated distancing/approaching linear acceleration is greater than said threshold linear acceleration.

* * * * *